United States Patent
Royer et al.

(10) Patent No.: US 11,332,724 B2
(45) Date of Patent: May 17, 2022

(54) MICROBIAL PRODUCTION OF TERPENOIDS

(71) Applicants: DSM IP ASSETS B.V., Heerlen (NL); John Royer, Lexington, MA (US); Peter Louis Houston, Boston, MA (US)

(72) Inventors: John Royer, Lexington, MA (US); Peter Louis Houston, Boston, MA (US)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/567,112

(22) PCT Filed: Apr. 21, 2016

(86) PCT No.: PCT/US2016/028549
§ 371 (c)(1),
(2) Date: Oct. 17, 2017

(87) PCT Pub. No.: WO2016/172282
PCT Pub. Date: Oct. 27, 2016

(65) Prior Publication Data
US 2018/0148697 A1 May 31, 2018

Related U.S. Application Data

(60) Provisional application No. 62/150,402, filed on Apr. 21, 2015, provisional application No. 62/150,549, filed on Apr. 21, 2015.

(51) Int. Cl.
| | | |
|---|---|---|
| C12N 9/10 | (2006.01) | |
| C12P 19/44 | (2006.01) | |
| A23L 27/30 | (2016.01) | |
| C07H 15/24 | (2006.01) | |
| C12N 9/02 | (2006.01) | |

(52) U.S. Cl.
CPC ............ C12N 9/1085 (2013.01); A23L 27/33 (2016.08); C07H 15/24 (2013.01); C12N 9/0042 (2013.01); C12P 19/44 (2013.01); C12Y 106/02004 (2013.01); C12Y 205/01 (2013.01); C12Y 205/01001 (2013.01); *A23V 2002/00* (2013.01)

(58) Field of Classification Search
CPC ..... C12N 9/1085; C12N 9/0042; A23L 27/33; C07H 15/24; C12Y 106/02004; C12Y 205/01; C12Y 205/01001; C12P 19/44; A23V 2002/00
See application file for complete search history.

(56) References Cited

U.S. PATENT DOCUMENTS

| | | | |
|---|---|---|---|
| 7,851,199 B2 | 12/2010 | Bailey et al. | |
| 2004/0072323 A1 | 4/2004 | Matsuda et al. | |
| 2012/0149886 A1 | 6/2012 | Bailey et al. | |
| 2013/0224809 A1* | 8/2013 | Bohlmann | C12N 9/88 435/127 |
| 2018/0132515 A1* | 5/2018 | Lawrence | A23L 27/33 |

FOREIGN PATENT DOCUMENTS

| | | |
|---|---|---|
| WO | WO 2006/102342 | 9/2006 |
| WO | WO 2008/042338 | 4/2008 |
| WO | WO 2008/128159 | 10/2008 |

OTHER PUBLICATIONS

Murphy et al. Functional characterization of two class II diterpene synthases indicates additional specialized diterpenoid pathways in maize (*Zea mays*). Frontiers in Plant Science (2018), vol. 9, Article 1542, p. 1-12.*
International Search Report for PCT/US2016/028549, dated Aug. 7, 2016, 1 page.
Written Opinion of the ISA for PCT/US2016/028549, dated Aug. 7, 2016, 5 pages.
RPD Csernetics et al., "Expression of three isoprenoid biosynthesis genes and their effects on the carotenoid production of the zygomycete", *Fungal Genetics and Biology*, vol. 48, No. 7, Mar. 21, 2011.
Antonio Velayos et al., "Expression of the carG gene, encoding geranylgeranyl pyrophosphate synthase, is up-regulated by blue light in Mucor circinelloides", *Current Genetics*, vol. 43, No. 2, May 1, 2003, pp. 112-120.
Misawa et al., "Structure and Functional Analysis of a Marine Bacterial Carotenoid Biosynthesis Gene Cluster and Astaxanthin Biosynthetic Pathway Proposed at the Gene Level" Journal of Bacteriology 177(22): 6575-6584 (1995).

* cited by examiner

*Primary Examiner* — Iqbal H Chowdhury
(74) *Attorney, Agent, or Firm* — Nixon & Vanderhye, PC

(57) ABSTRACT

The present invention provides genetically engineered host organisms capable of producing terpenoids. The present invention also relates terpenoids obtained from such genetically engineered organisms. Examples of the produced terpenoids include carotenoids, ionones, abienol, and other isoprenoid derived compounds. In addition, the invention relates to a methods of for the preparation of terpenoids using such a genetically engineered organism.

9 Claims, 7 Drawing Sheets
Specification includes a Sequence Listing.

MEVALONATE PATHWAY TO ISOPRENOIDS

SEQUENCE LISTING

```
<160> NUMBER OF SEQ ID NOS: 3

<210> SEQ ID NO 1
<211> LENGTH: 909
<212> TYPE: DNA
<213> ORGANISM: Mucor Circinelloides

<400> SEQUENCE: 1
atgctcaact cacacaacag aaccgaagaa agatcgaccg aagacatcat tttggagcct      60
tacacctact tgatatcaca gcctggcaaa gatatccggg caaagttaat ttcggcattc     120
gacctgtggc tgcatgtgcc caaggacgtg ctgtgcgtaa tcaacaagat tatcggcatg     180
ttgcataatg ctagtttaat gatcgacgat gtgcaggatg actctgatct tcgaagaggt     240
gtgcctgtcg ctcaccatat ttatggtgta cctcagacta tcaacactgc aaattatgtc     300
atcttcttgg cattgcaaga agtgatgaag ctgaacatcc ccagcatgat gcaagtgtgc     360
acggaagagc tgatcaatct gcatcgaggc cagggcatcg agctgtactg gagagacagc     420
ctgacttgcc ccaccgaaga agagtacatt gatatggtca acaacaaaac cagcggttta     480
ttacgattgg cggtgcgatt aatgcaagca gcaagtgaaa gtgacattga ttacacaccg     540
ctcgtcaaca ttataggcat ccatttccag gtgcgcgatg actacatgaa cttgcaatcc     600
accagctata caaacaacaa gggcttttgt gaggatctga cagagggcaa gtttcatttt     660
cccatcattc atgccatcag aaaggaccct tccaaccgcc aactgctcaa catcatcagc     720
cagaagccca catccattga agtcaaaaag tatgcattgg aggtgattcg caaggcaggc     780
agttttgaat acgtgcgcga gtttctgcgt caaaagagg ccgagtcttt gaaggaaatc     840
aagcgtttgg gtggtaatcc tttgctggaa aagtacattg agaccatcag agtagaggcc     900
``` accaacgac                                                                                            909

<210> SEQ ID NO 2
<211> LENGTH: 303
<212> TYPE: PRT
<213> ORGANISM: Mucor Circinelloides

<400> SEQUENCE: 2

Met Leu Asn Ser His Asn Arg Thr Glu Glu Arg Ser Thr Glu Asp Ile
1               5                   10                  15

Ile Leu Glu Pro Tyr Thr Tyr Leu Ile Ser Gln Pro Gly Lys Asp Ile
            20                  25                  30

Arg Ala Lys Leu Ile Ser Ala Phe Asp Leu Trp Leu His Val Pro Lys
        35                  40                  45

Asp Val Leu Cys Val Ile Asn Lys Ile Ile Gly Met Leu His Asn Ala
    50                  55                  60

Ser Leu Met Ile Asp Asp Val Gln Asp Ser Asp Leu Arg Arg Gly
65                  70                  75                  80

Val Pro Val Ala His His Ile Tyr Gly Val Pro Gln Thr Ile Asn Thr
                85                  90                  95

Ala Asn Tyr Val Ile Phe Leu Ala Leu Gln Glu Val Met Lys Leu Asn
            100                 105                 110

Ile Pro Ser Met Met Gln Val Cys Thr Glu Glu Leu Ile Asn Leu His
        115                 120                 125

Arg Gly Gln Gly Ile Glu Leu Tyr Trp Arg Asp Ser Leu Thr Cys Pro
    130                 135                 140

Thr Glu Glu Glu Tyr Ile Asp Met Val Asn Asn Lys Thr Ser Gly Leu
145                 150                 155                 160

Leu Arg Leu Ala Val Arg Leu Met Gln Ala Ala Ser Glu Ser Asp Ile
                165                 170                 175

Asp Tyr Thr Pro Leu Val Asn Ile Ile Gly Ile His Phe Gln Val Arg
            180                 185                 190

Asp Asp Tyr Met Asn Leu Gln Ser Thr Ser Tyr Thr Asn Asn Lys Gly
        195                 200                 205

Phe Cys Glu Asp Leu Thr Glu Gly Lys Phe Ser Phe Pro Ile Ile His
    210                 215                 220

Ala Ile Arg Lys Asp Pro Ser Asn Arg Gln Leu Leu Asn Ile Ile Ser
225                 230                 235                 240

Gln Lys Pro Thr Ser Ile Glu Val Lys Lys Tyr Ala Leu Glu Val Ile
                245                 250                 255

Arg Lys Ala Gly Ser Phe Glu Tyr Val Arg Glu Phe Leu Arg Gln Lys
            260                 265                 270

Glu Ala Glu Ser Leu Lys Glu Ile Lys Arg Leu Gly Gly Asn Pro Leu
        275                 280                 285

Leu Glu Lys Tyr Ile Glu Thr Ile Arg Val Glu Ala Thr Asn Asp
    290                 295                 300

<210> SEQ ID NO 3
<211> LENGTH: 909
<212> TYPE: DNA
<213> ORGANISM: Mucor Circinelloides

<400> SEQUENCE: 3
atgctcaact ctcacaaccg aaccgaggag cgatccaccg aggatattat tctcgagcct        60
tacacctacc tcatttctca gcccggaaag gacattcgag ctaagctcat ttctgccttt       120

```
gacctctggc tgcacgttcc taaggatgtt ctttgcgtca tcaacaagat tatcggtatg    180
ctgcacaacg cctctcttat gattgacgat gttcaggacg actctgatct ccgacgagga    240
gtccccgttg ctcaccacat ttacggtgtc cctcagacta ttaacaccgc taactacgtg    300
attttcctcg cccttcagga ggttatgaag ctgaacatcc cttctatgat gcaggtgtgt    360
accgaggagc ttattaacct ccaccgaggt cagggaattg agctgtactg gcgagattcc    420
ctcacttgtc ccactgagga ggagtacatt gatatggtta acaacaagac ctctggcctc    480
cttcgacttg ccgtccgact gatgcaggct gcttctgagt ccgacatcga ctacacccct    540
ctcgtcaaca ttatcggaat tcacttccag gttcgagatg actacatgaa cctccagtcc    600
acctcttaca ctaacaacaa gggcttttgc gaggacctga ccgagggaaa gttctccttc    660
cctattattc acgctattcg aaaggacccc tctaaccgac agctcctgaa cattatctct    720
cagaagccca cctccattga ggttaagaag tacgctcttg aggtgatccg aaaggctgga    780
tcttttgagt acgttcgaga gttccttcga cagaaggagg ctgagtccct gaaggagatc    840
aagcgacttg gcggcaaccc tctcctcgag aagtacattg agactattcg agtcgaggct    900
actaacgac                                                            909
```

MICROBIAL PRODUCTION OF TERPENOIDS

CROSS-REFERENCE TO RELATED APPLICATIONS

This application is the U.S. national phase of International Application No. PCT/US2016/028549 filed Apr. 21, 2016 which designated the U.S. and claims the benefit of the filing date of U.S. Provisional Application No. 62/150,402 filed Apr. 21, 2015 and Provisional Patent Application No. 62/150,549 filed Apr. 21, 2015, the entire contents of which are hereby incorporated by reference.

FIELD OF THE INVENTION

The present invention provides genetically engineered host organisms capable of producing terpenoids. The present invention also relates to terpenoids obtained from such genetically engineered organisms. Examples of the produced terpenoids include carotenoids, ionones, abienol, and other isoprenoid derived compounds. In addition, the invention relates to a method for the preparation of terpenoids using such a genetically engineered organism.

BACKGROUND OF THE INVENTION

Terpenoids are a large and diverse class of naturally occurring organic chemicals. They are derived from five-carbon isoprene units assembled and modified in thousands of ways. Carotenoids represent a large class of terpenoids. Carotenoids are organic pigments ranging in color from yellow to red that are produced by certain organisms, including photosynthetic organisms as well as some bacteria and fungi. Carotenoids are responsible for the vivid yellow, orange, or red color in plants such as carrots, peppers, tomatoes, and animals such as salmon, lobster and shrimps, as well as many birds. Carotenoids have important functions in photosynthesis, nutrition, and protection against photo oxidative damages.

A large number of aroma ingredients are also derived from terpenoids. Examples of such aroma ingredients include the diterpene ambrox and its precursors such as sclareol and abienol. Ambrox is a substitute for ambergris which is a traditional fragrance ingredient. Ionones are another group of aroma ingredients that are derived from terpenoids.

Ionones are aroma compounds found in a variety of essential oils, including rose oil. β-ionone is a significant contributor to the aroma of roses, and is an important fragrance chemical used in perfumery. Ionones are derived from carotenoids.

Structurally, terpenoids are hydrocarbons resulting from the combination of several isoprene units. For example, carotenoids are 40-carbon terpenoids derived from eight 5-carbon isoprene building blocks. Sclareol and abienol are 20-carbon terpenoids derived from four 5-carbon isoprene building blocks.

The biosynthetic pathway of terpenoids can be divided into two portions: the upper isoprenoid biosynthesis pathway, which leads to the formation of 20-carbon geranylgeranyl pyrophasphate GGPP, and the lower terpenoid biosynthesis pathway, which converts GGPP into various terpenoid compounds. See FIGS. 1B-1D. The portion of the upper isoprenoid pathway involving the condensation of five-carbon units to create GGPP is shown in FIG. 1A.

Although several thousand terpenoids have been identified in nature, only a few are produced industrially for food coloring, nutritional additives, pharmaceuticals and cosmetics. Presently, most of the terpenoids used for industrial purposes are produced by chemical synthesis. However, some compounds are very difficult to produce chemically. Attempts to make terpenoids via fermentation have been made and are showing early progress (U.S. Pat. No. 7,851,199).

A number of carotenoids have been produced from microbial sources. For example, β-carotene has been produced from *E. coli* and *Yarrowia lipolytica*. Zeaxanthin and astaxanthin have been produced from *E. coli, Candida utilis*, and *Yarrowia lipolytica*.

The genes encoding various elements of the terpenoid biosynthesis pathway have been identified. Such genes have been cloned and expressed in various microbes. For example, genes encoding HMG-CoA reductase, and GGPP synthase have been isolated from *Yarrowia lipolytica, Mucor circinelloides*, and *Saccharomyces cerevisiae*, and have been expressed in host cells such as *E. coli* and *Yarrowia lipolytica*.

The chemical methods for producing terpenoids available to date, however, suffer from low yields and reliance on expensive precursors. A method that produces higher yields of terpenoids from inexpensive precursors is clearly needed.

SUMMARY OF THE INVENTION

The present invention is directed to a genetically modified host microorganism comprising a polynucleotide molecule encoding a geranylgeranyl pyrophosphate (GGPP) synthase that produces at least one terpenoid, wherein the polynucleotide molecule is selected from the group consisting of: (a) a nucleic acid molecule comprising a polynucleotide sequence encoding a protein having the amino acid sequence of SEQ ID NO:2; (b) a nucleic acid molecule comprising a polynucleotide sequence encoding a protein having an amino acid sequence with substitution, deletion, insertion and/or addition of one or several amino acid residues in the amino acid sequence of SEQ ID NO:2, wherein the protein having GGPP synthase activity; and (c) a nucleic acid molecule comprising a polynucleotide sequence encoding a protein having at least 90% identity to the amino acid sequence of SEQ ID NO:2, wherein the protein having GGPP synthase activity.

In some embodiments, the genetically modified microorganism has an increased GGPP synthase activity compared with the same microorganism without said polynucleotide molecule. In some embodiments, the genetically modified microorganism produces enhanced amount of terpenoids compared with the same microorganism without said polynucleotide molecule. In certain embodiment, the terpenoids are derived from GGPP. In some embodiments, the terpenoids can also be selected from the group consisting of: carotenoids, ionones, sclareol and abienol.

In some embodiments, the genetically modified microorganism may further comprises one or more recombinant nucleotide sequence(s) encoding isoprenoid biosynthesis polypeptides, isoprenoid biosynthesis competitor polypeptides, and/or carotenoid biosynthesis polypeptides. Examples of the polypeptides include, but are not limited to, a polypeptide having phytoene synthase activity, a polypeptide having phytoene dehydrogenase activity, a polypeptide having lycopene beta-cyclase activity, a polypeptide having lycopene epsilon-cyclase activity, and a polypeptide having carotenoid cleavage dioxygenase activity.

In some embodiments, the genetically modified microorganism may further comprises one or more recombinant nucleotide sequence(s) encoding a polypeptide having class I diterpene synthase activity, a polypeptide having class I diterpene synthase activity, and/or a polypeptide having class I/II diterpene synthase activity.

The genetically modified microorganism of present invention may be a fungus or a bacterium. Example microorgansims include, but are not limited to, *Yarrowia* fungus, *Saccharomyces cerevisiae*, and *E. coli*.

The present invention is directed to a method to produce at least one terpenoids, comprising: expressing a GGPP synthase gene in a host cell under conditions effective to produce terpenoids, wherein the GGPP synthase gene comprises the above mentioned recombinant nucleic acid molecules in the host cell, and wherein at least one terpenoid is produced.

The present invention is also directed to the terpenoids obtained from the above mentioned genetically modified microorganism.

The present invention is also directed to food products or feeds comprising the terpenoid obtained from the genetically modified microorganism described above.

The present invention is also directed to fragrances or cosmetic products comprising the terpenoid obtained from the genetically modified microorganism described above.

BRIEF DESCRIPTION OF THE DRAWINGS/FIGURES

Figure 3:
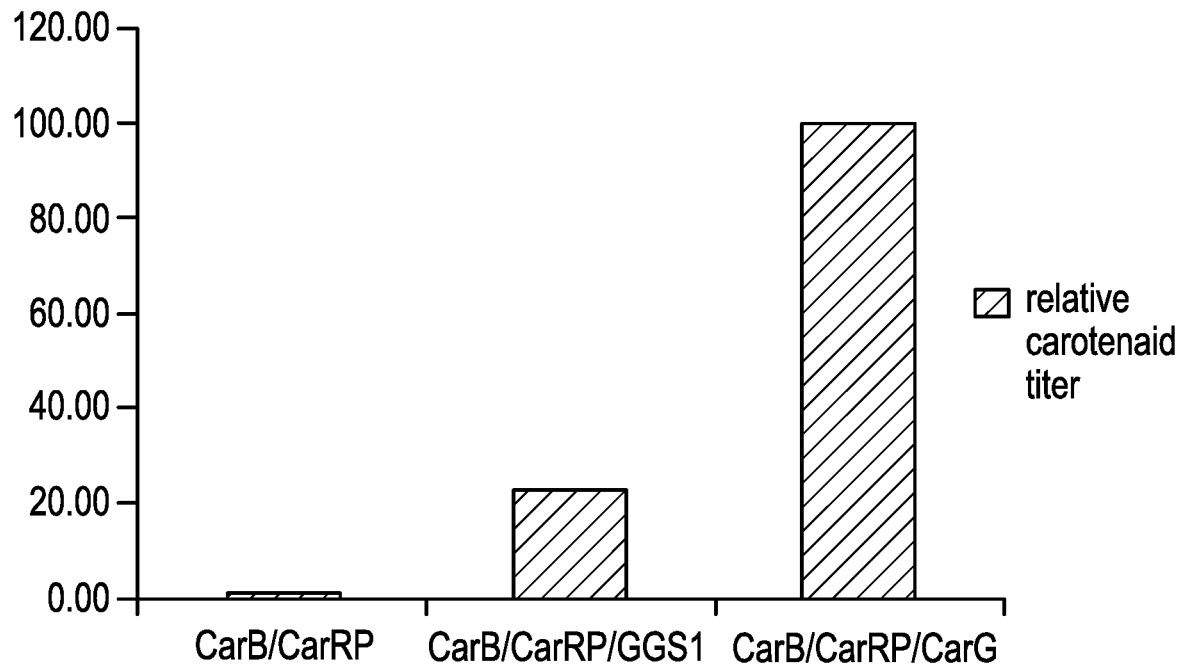

FIG. 3 shows the comparison of carotenoid production among three *Yarrowia* strains: a) one strain transformed with the carB and carRP genes from *Mucor circinelloides*, b) another transformed with the carB and carRP genes from *Mucor circinelloides* and one copy of the GGS1 gene from *Yarrowia lipolytica*, and c) a third one transformed with the carB, carRP, and carG genes from *Mucor circinelloides*.

Figure 4:
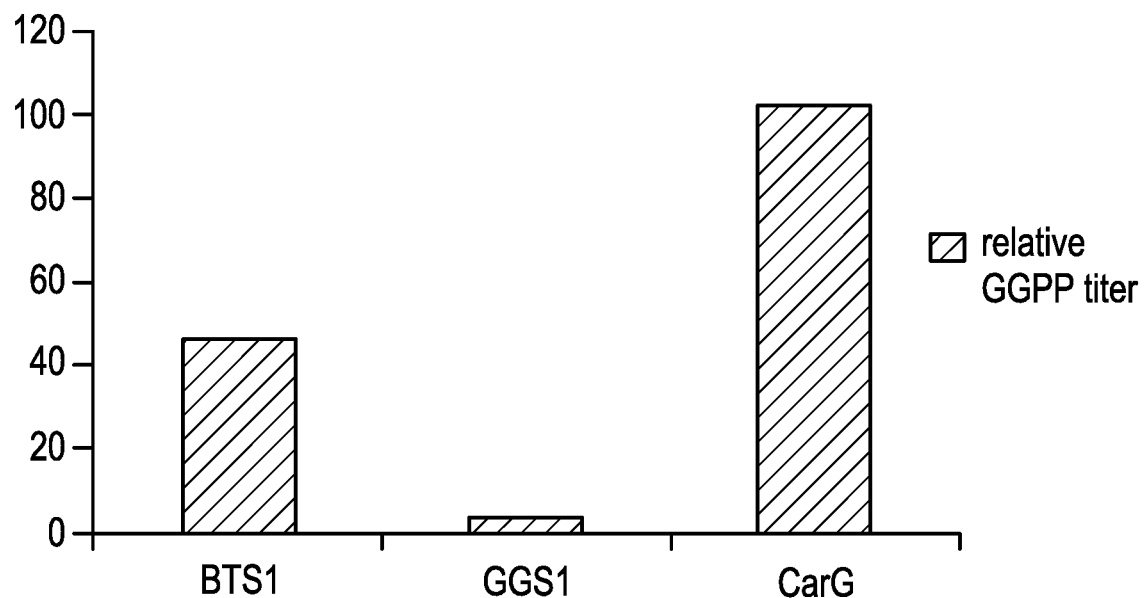

FIG. 4 shows the comparison of GGPP production among three *Saccharomyces cerevisiae* strains: a) a genetically modified *Saccharomyces cerevisiae* strain overexpressing the BTS1 gene (the *S. cerivisae* gene encoding Ggs), b) a genetically modified *Saccharomyces cerevisiae* strain overexpressing the GGS1 gene from *Yarrowia lipolytica*, and c) a genetically modified *Saccharomyces cerevisiae* strain overexpressing the carG gene from *Mucor circinelloides*.

Figure 5:
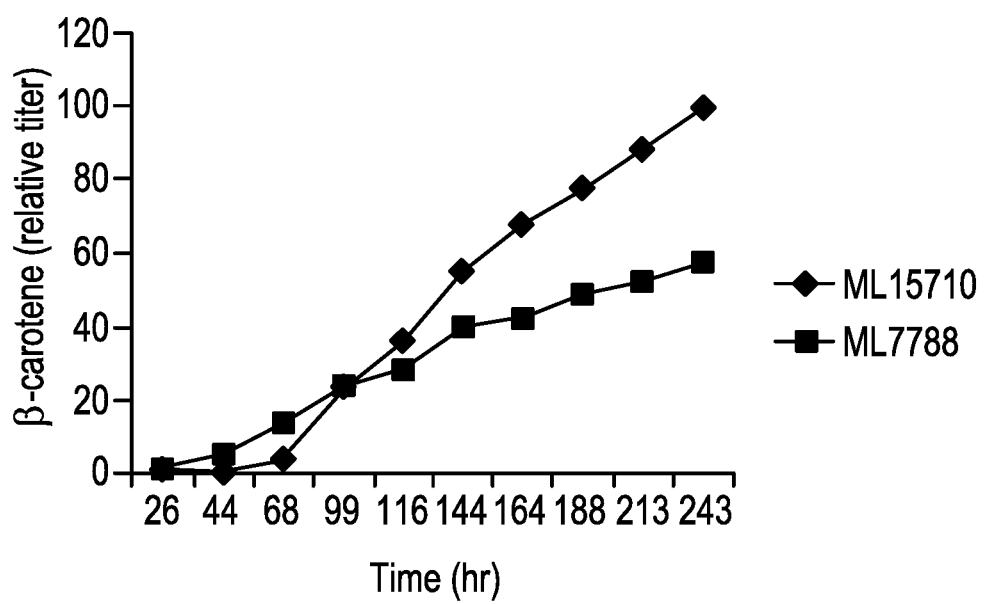

FIG. 5. shows the comparison of β-carotene production between *Yarrowia lipolytica* strain ML7788 and the same strain harboring the carG gene (new strain ML15710), in lab scale fermenters.

Figure 6:
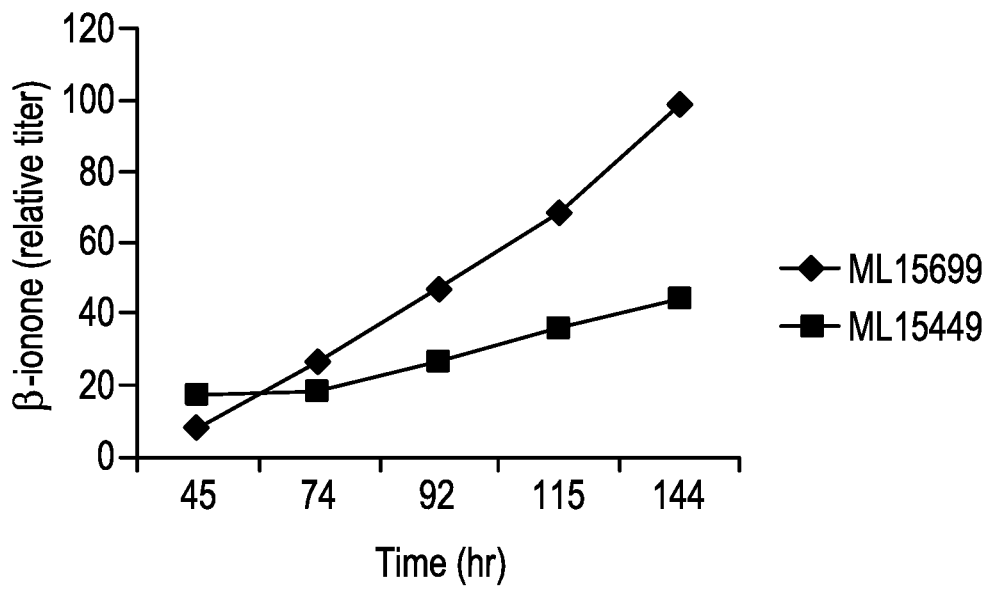

FIG. 6. shows the comparison of ionone production between a *Yarrowia lipolytica* strain ML15449 and the same strain harboring the carG gene (new strain ML15699), in lab scale fermenters.

Figure 7:
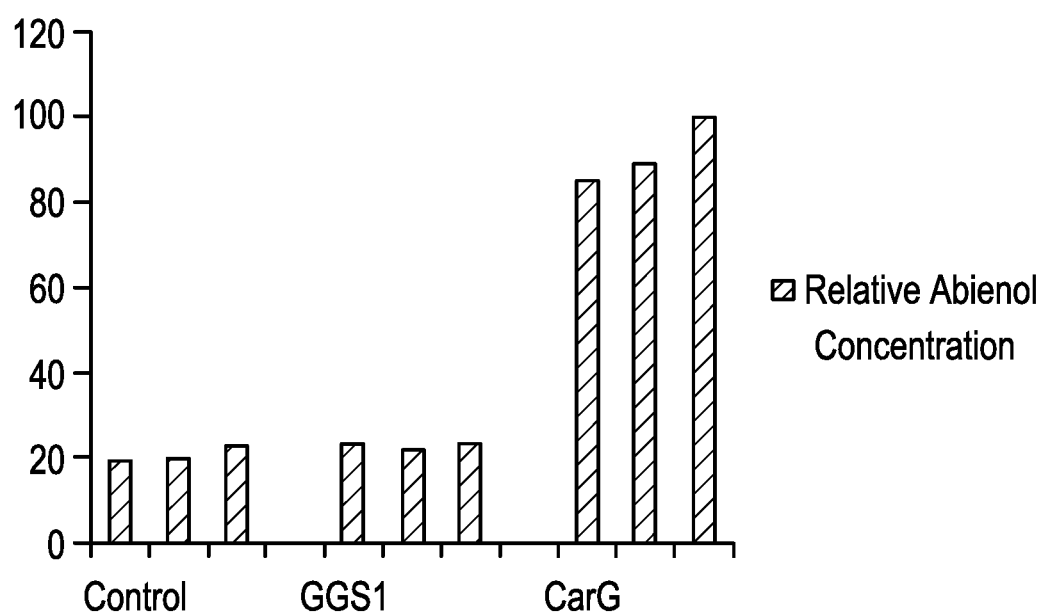

FIG. 7. shows the comparison of abienol production between a genetically modified *Yarrowia lipolytica* strain transformed with multiple copies of GGS1 gene from *Yarrowia lipolytica* and another *Yarrowia lipolytica* strain transformed with the carG gene from *Mucor circinelloides* as well as multiple copies of GGS1, in shake plate culture.

OVERVIEW OF THE SEQUENCE LISTING

The nucleic acid sequences in the accompanying sequence list are shown using standard letter abbreviation for nucleotide bases. Only one strand of each nucleic acid sequence is shown, but the complementary strand is understood to be included by any reference to the displayed strand. In the accompanying sequence listing:

```
SEQ ID NO: 1 is the DNA sequence encoding the
geranylgeranyl pyrophosphate synthase gene (carG)
from Mucor circinelloides.
atgctcaactcacacaacagaaccgaagaaagatcgaccgaagacatcat tttggagccttacacctacttgatatcacagcctggcaaagatatccggg caaagttaatttcggcattcgacctgtggctgcatgtgcccaaggacgtg ctgtgcgtaatcaacaagattatcggcatgttgcataatgctagtttaat gatcgacgatgtgcaggatgactctgatcttcgaagaggtgtgcctgtcg ctcaccatatttatggtgtacctcagactatcaacactgcaaattatgtc atcttcttggcattgcaagaagtgatgaagctgaacatccccagcatgat gcaagtgtgcacggaagagctgatcaatctgcatcgaggccagggcatcg agctgtactggagagacagcctgacttgccccaccgaagaagagtacatt gatatggtcaacaacaaaaccagcggtttattacgattggcggtgcgatt aatgcaagcagcaagtgaaagtgacattgattacacaccgctcgtcaaca ttataggcatccatttccaggtgcgcgatgactacatgaacttgcaatcc accagctatacaaacaacaagggctatgtgaggatctgacagagggcaag ttttcatttcccatcattcatgccatcagaaaggacccttccaaccgcca actgctcaacatcatcagccagaagcccacatccattgaagtcaaaaagt atgcattggaggtgattcgcaaggcaggcagttttgaatacgtgcgcgag tttctgcgtcaaaaagaggccgagtctttgaaggaaatcaagcgtttggg tggtaatcctttgctggaaaagtacattgagaccatcagagtagaggcca ccaacgac SEQ ID NO: 2 is the amino acid sequence encoding
the geranylgeranyl pyrophosphate synthase
(carG) from Mucor circinelloides.
MLNSHNRTEERSTEDIILEPYTYLISQPGKDIRAKLISAFDLWLHVPKDV

LCVINKIIGMLHNASLMIDDVQDDSDLRRGVPVAHHIYGVPQTINTANYV

IFLALQEVMKLNIPSMMQVCTEELINLHRGQGIELYWRDSLTCPTEEEVI

DMVNNKTSGLLRLAVRLMQAASESDIDYTPLVNIIGIHFQVRDDYMNLQS

TSYTNNKGFCEDLTEGKFSFPIIHAIRKDPSNRQLLNIISQKPTSIEVKK

YALEVIRKAGSFEYVREFLRQKEAESLKEIKRLGGNPLLEKYIETIRVEA

TND
```

-continued

SEQ ID NO: 3 is the DNA sequence encoding the geranylgeranyl pyrophosphate synthase gene (carG) from Mucor circinelloides, as optimized for expression in Yarrowia lipolynca.

atgctcaactctcacaaccgaaccgaggagcgatccaccgaggatattat tctcgagccttacacctacctcatttctcagcccggaaaggacattcgag ctaagctcatttctgcctttgacctctggctgcacgttcctaaggatgtt ctttgcgtcatcaacaagattatcggtatgctgcacaacgcctctcttat gattgacgatgttcaggacgactctgatctccgacgaggagtccccgttg ctcaccacatttacggtgtccctcagactattaacaccgctaactacgtg attttcctcgcccttcaggaggttatgaagctgaacatcccttctatgat gcaggtgtgtaccgaggagcttattaacctccaccgaggtcagggaattg agctgtactggcgagattccctcacttgtcccactgaggaggagtacatt gatatggttaacaacaagacctctggcctccttcgacttgccgtccgact gatgcaggctgcttctgagtccgacatcgactacacccctctcgtcaaca ttatcggaattcacttccaggttcgagatgactacatgaacctccagtcc acctcttacactaacaacaagggcttagcgaggacctgaccgagggaaag ttctccttccctattattcacgctattcgaaaggaccctctaaccgaca gctcctgaacattatctctcagaagcccacctccattgaggttaagaagt acgctcttgaggtgatccgaaaggctggatcttttgagtacgttcgagag ttccttcgacagaaggaggctgagtccctgaaggagatcaagcgacttgg cggcaaccctctcctcgagaagtacattgagactattcgagtcgaggcta ctaacgac Definitions Carotenogenic modification: The term "carotenogenic modification", as used herein, refers to a modification of a host organism that adjusts production of one or more carotenoids, as described herein. For example, a carotenogenic modification may increase the production level of one or more carotenoids, and/or may alter relative production levels of different carotenoids. In principle, a carotenogenic modification may be any chemical, physiological, genetic, or other modification that appropriately alters production of one or more carotenoids in a host organism produced by that organism as compared with the level produced in an otherwise identical organism not subject to the same modification. In most embodiments, however, the carotenogenic modification will comprise a genetic modification, typically resulting in increased production of one or more selected carotenoids. In some embodiments, the carotenogenic modification comprises at least one chemical, physiological, genetic, or other modification; in other embodiments, the carotenogenic modification comprises more than one chemical, physiological, genetic, or other modification. In certain aspects where more than one modification is utilized, such modifications can comprise any combination of chemical, physiological, genetic, or other modification (e.g., one or more genetic, chemical, and/or physiological modification(s)). In some embodiments, the selected carotenoid is one or more of astaxanthin, β-carotene, canthaxanthin, lutein, lycopene, phytoene, zeaxanthin, and/or modifications of zeaxanthin or astaxanthin (e.g., glucoside, esterified zeaxanthin or astaxanthin). In some embodiments, the selected carotenoid is one or more xanthophylls, and/or a modification thereof (e.g., glucoside, esterified xanthophylls). In certain embodiments, the selected xanthophyl is selected from the group consisting of astaxanthin, lutein, zeaxanthin, lycopene, and modifications thereof.

Carotenogenic polypeptide: The term "carotenogenic polypeptide", as used herein, refers to any polypeptide that is involved in the process of producing carotenoids in a cell, and may include polypeptides that are involved in processes other than carotenoid production but whose activities affect the extent or level of production of one or more carotenoids, for example by scavenging a substrate or reactant utilized by a carotenoid polypeptide that is directly involved in carotenoid production. Carotenogenic polypeptides include isoprenoid biosynthesis polypeptides, carotenoid biosynthesis polypeptides, and isoprenoid biosynthesis competitor polypeptides, as those terms are defined herein. The term also encompasses polypeptides that may affect the extent to which carotenoids are accumulated in lipid bodies.

Carotenoid: The term "carotenoid" is understood in the art to refer to a structurally diverse class of pigments derived from isoprenoid pathway intermediates. The commitment step in carotenoid biosynthesis is the formation of phytoene from geranylgeranyl pyrophosphate. Carotenoids can be acyclic or cyclic, and may or may not contain oxygen, so that the term carotenoids include both carotenes and xanthophylls. In general, carotenoids are hydrocarbon compounds having a conjugated polyene carbon skeleton formally derived from the five-carbon compound IPP, including triterpenes ($C_{30}$ diapocarotenoids) and tetraterpenes ($C_{40}$ carotenoids) as well as their oxygenated derivatives and other compounds that are, for example, $C_{35}$, $C_{50}$, $C_{60}$, $C_{70}$, $C_{80}$ in length or other lengths. Many carotenoids have strong light absorbing properties and may range in length in excess of $C_{200}$. $C_{30}$ diapocarotenoids typically consist of six isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{30}$ carotenoids may be formally derived from the acyclic $C_{30}H_{42}$ structure, having a long central chain of conjugated double bonds, by: (i) hydrogenation (ii) dehydrogenation, (iii) cyclization, (iv) oxidation, (v) esterification/glycosylation, or any combination of these processes. $C_{40}$ carotenoids typically consist of eight isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{40}$ carotenoids may be formally derived from the acyclic $C_{40}H_{56}$ structure, having a long central chain of conjugated double bonds, by (i) hydrogenation, (ii) dehydrogenation, (iii) cyclization, (iv) oxidation, (v) esterification/glycosylation, or any combination of these processes. The class of $C_{40}$ carotenoids also includes certain compounds that arise from rearrangements of the carbon skeleton, or by the (formal) removal of part of this structure. More than 600 different carotenoids have been identified in nature. Carotenoids include but are not limited to: antheraxanthin, adonirubin, adonixanthin, astaxanthin, canthaxanthin, capsorubrin, β-cryptoxanthin, α-carotene, β-carotene, δ-carotene, ε-carotene, echinenone, 3-hydroxyechinenone, 3'-hydroxyechinenone, γ-carotene, lycopene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, rhodoxanthin, and C30 carotenoids. Additionally, carotenoid compounds include derivatives of these molecules, which may include hydroxy-, methoxy-, oxo-, epoxy-, carboxy-, or aldehydic functional groups. Further, included carotenoid compounds include esters (e.g., fatty acid ester), ethers (e.g., glycosides) and sulfate derivatives (e.g., esterified xanthophylls).

Carotenoid biosynthesis polypeptide: The term "carotenoid biosynthesis polypeptide" refers to any polypeptide that is involved in the synthesis of one or more carotenoids. To mention but a few, these carotenoid biosynthesis polypeptides include, for example, polypeptides of phytoene synthase, phytoene dehydrogenase (or desaturase), lycopene cyclase, carotenoid ketolase, carotenoid hydroxylase, astaxanthin synthase, carotenoid epsilon hydroxylase, lycopene cyclase (beta and epsilon subunits), carotenoid glucosyltransferase, and acyl CoA:diacyglycerol acyltransferase, and alcohol acetyl transferase. In some instances, a single gene may encode a protein with multiple carotenoid biosynthesis polypeptide activities. As will be appreciated by those of ordinary skill in the art, in some embodiments of the disclosure, carotenoid biosynthesis polypeptides include polypeptides that affect the expression and/or activity of one or more other carotenoid biosynthesis polypeptides.

Isoprenoid: The term "isoprenoid" refers to any compound which is derived via the pathway beginning with isopentenyl pyrophosphate (IPP) and formed by the head-to-tail condensation of isoprene units which may be, in one embodiment, of 5, or, in another embodiment, of 10, or, in another embodiment, of 15, or, in another embodiment, of 20, or, in another embodiment, of 30, or, in another embodiment, of 40 carbons in length.

Isoprenoid biosynthesis competitor: The term "isoprenoid biosynthesis competitor", as used herein, refers to an agent whose presence or activity in a cell reduces the level of geranylgeranyl diphosphate (GGPP) available to enter the carotenoid biosynthesis pathway. The term "isoprenoid biosynthesis competitor" encompasses both polypeptide and non-polypeptide (e.g., small molecule) inhibitor agents. Those of ordinary skill in the art will appreciate that certain competitor agents that do not act as inhibitors of isoprenoid biosynthesis generally can nonetheless act as inhibitors of biosynthesis of a particular isoprenoid compound. Particular examples of isoprenoid biosynthesis competitor agents act on isoprenoid intermediates prior to GGPP, such that less GGPP is generated. Squalene synthase is but one isoprenoid biosynthesis competitor polypeptide according to the present disclosure. Prenyldiphosphate synthase enzymes and para-hydroxybenzoate (PHB) polyprenyltransferase are yet additional isoprenoid biosynthesis competitor polypeptides according to the present disclosure. In certain embodiments, one or more polypeptide components of the SAGA complex are isoprenoid biosynthesis competitors according to the present disclosure. Those of ordinary skill in the art, considering the known metabolic pathways relating to isoprenoid production and/or metabolism will readily appreciate a variety of other particular isoprenoid biosynthesis competitors, including isoprenoid biosynthesis polypeptides.

Isoprenoid biosynthesis polypeptide: The term "isoprenoid biosynthesis polypeptide" refers to any polypeptide that is involved in the synthesis of isoprenoids. For example, as discussed herein, acetoacetyl-CoA thiolase, HMG-CoA synthase, HMG-CoA reductase, mevalonate kinase, phosphomevalonate kinase, mevalonate pyrophosphate decarboxylase, IPP isomerase, FPP synthase, and GGPP synthase, are all involved in the mevalonate pathway for isoprenoid biosynthesis. Each of these proteins is also an isoprenoid biosynthesis polypeptide for purposes of the present disclosure. As will be appreciated by those of ordinary skill in the art, in some embodiments of the disclosure, isoprenoid biosynthesis polypeptides include polypeptides that affect the expression and/or activity of one or more other isoprenoid biosynthesis polypeptides (e.g., of one or more enzymes that participates in isoprenoid synthesis). Thus, for instance, transcription factors that regulate expression of isoprenoid biosynthesis enzymes can be isoprenoid biosynthesis polypeptides for purposes of the present disclosure.

Isoprenoid pathway: The term "isoprenoid pathway" is understood in the art to refer to a metabolic pathway that either produces or utilizes the five-carbon metabolite isopentyl pyrophosphate (IPP). As discussed herein, two different pathways can produce the common isoprenoid precursor IPP—the "mevalonate pathway" and the "non-mevalonate pathway". The term "isoprenoid pathway" is sufficiently general to encompass both of these types of pathway. Biosynthesis of isoprenoids from IPP occurs by polymerization of several five-carbon isoprene subunits. Isoprenoid metabolites derived from IPP are of varying size and chemical structure, including both cyclic and acyclic molecules. Isoprenoid metabolites include, but are not limited to, monoterpenes, sesquiterpenes, diterpenes, sterols, and polyprenols such as carotenoids.

The terms "polynucleotide" and "nucleic acid" are intended to encompass a singular nucleic acid as well as plural nucleic acids, a nucleic acid molecule or fragment, variant, or derivative thereof, or construct, e.g., messenger RNA (mRNA) or plasmid DNA (pDNA). A polynucleotide or nucleic acid can contain the nucleotide sequence of the full-length cDNA sequence, or a fragment thereof, including the untranslated 5' and 3' sequences and the coding sequences. A polynucleotide or nucleic acid can be composed of any polyribonucleotide or polydeoxyribonucleotide, which can be unmodified RNA or DNA or modified RNA or DNA. For example, a polynucleotide or nucleic acid can be composed of single- and double-stranded DNA, DNA that is a mixture of single- and double-stranded regions, single- and double-stranded RNA, and RNA that is a mixture of single- and double-stranded regions, hybrid molecules comprising DNA and RNA that can be single-stranded or, more typically, double-stranded or a mixture of single- and double-stranded regions. These terms also embrace chemically, enzymatically, or metabolically modified forms of a polynucleotide or nucleic acid.

The term "gene" refers to a nucleic acid or fragment thereof that is capable of being expressed as a specific protein, optionally including regulatory sequences preceding (5' non-coding sequences) and following (3' non-coding sequences) the coding sequence.

As used herein, the terms "polypeptide" is intended to encompass a singular "polypeptide" as well as plural "polypeptides" and fragments thereof, and refers to a molecule composed of monomers (amino acids) linearly linked by amide bonds (also known as peptide bonds). The term "polypeptide" refers to any chain or chains of two or more amino acids, and does not refer to a specific length of the product Thus, peptides, dipeptides, tripeptides, oligopeptides, protein, amino acid chain, or any other term used to refer to a chain or chains of two or more amino acids, are included within the definition of "polypeptide," and the term "polypeptide" can be used instead of, or interchangeably with any of these terms. A polypeptide can be derived from a natural biological source or produced by recombinant technology, but is not necessarily translated from a designated nucleic acid sequence. It can be generated in any manner, including by chemical synthesis.

As used herein, "native" refers to the form of a polynucleotide, gene or polypeptide as found in nature with its own regulatory sequences, if present.

As used herein, "endogenous" refers to the native form of a polynucleotide, gene or polypeptide in its natural location in the organism or in the genome of an organism. "Endogenous polynucleotide" includes a native polynucleotide in its natural location in the genome of an organism. "Endogenous gene" includes a native gene in its natural location in the genome of an organism. "Endogenous polypeptide" includes a native polypeptide in its natural location in the organism.

As used herein, "heterologous" refers to a polynucleotide, gene or polypeptide not normally found in the host organism but that is introduced into the host organism. "Heterologous polynucleotide" includes a native coding region, or portion thereof, that is reintroduced into the source organism in a form that is different from the corresponding native polynucleotide. "Heterologous gene" includes a native coding region, or portion thereof, that is reintroduced into the source organism in a form that is different from the corresponding native gene. For example, a heterologous gene can include a native coding region that is a portion of a chimeric gene including non-native regulatory regions that is reintroduced into the native host. "Heterologous polypeptide" includes a native polypeptide that is reintroduced into the source organism in a form that is different from the corresponding native polypeptide.

The term "genetically modified" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. The term "genetically modified" is synonymous with "recombinant".

The term "derivative" as used herein, refers to a modification of a sequence disclosed in the present invention. Illustrative of such modifications would be the substitution, insertion, and/or deletion of one or more bases relating to a nucleic acid sequence of a coding sequence disclosed herein that preserve, slightly alter, or increase the function of a coding sequence disclosed herein in the host organism.

The term "sequence identity" as used herein, refers to the relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the-nobrief option) is used as the percent identity and is calculated as follows:

(Identical Residues×100)/(Length of Alignment−
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

The term "control sequences" means all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

The term "operably linked" means a configuration in which a control sequence is placed at an appropriate position relative to the coding sequence of a polynucleotide such that the control sequence directs the expression of the coding sequence.

The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

The term "host organism" means unicellular or multicellular organism comprising the host cell.

The term "variant" means a polypeptide having enzyme activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

The term "promoter" refers to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths can have identical promoter activity.

The term "expression" as used herein, refers to the transcription and stable accumulation of sense (mRNA) or antisense RNA derived from the nucleic acid fragment of the invention. Expression can also refer to translation of mRNA into a polypeptide.

The term "overexpression" as used herein, refers to expression that is higher than endogenous expression of the same or related gene. A heterologous gene is overexpressed if its expression is higher than that of a comparable endogenous gene.

As used herein, the term "transformation" refers to the transfer of a nucleic acid or fragment into a host organism, resulting in genetically stable inheritance. Host organisms containing the transformed nucleic acid fragments are referred to as "transgenic" or "recombinant" or "transformed" organisms.

The terms "plasmid" and "vector" as used herein refer to an extra chromosomal element often carrying genes which are not part of the central metabolism of the cell, and usually in the form of circular double-stranded DNA molecules. Such elements can be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein, the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts refers to the alteration of codons in the gene or coding regions of the nucleic acid molecules to reflect the typical codon usage of the host organism without altering the polypeptide encoded by the DNA. Such optimization includes replacing at least one, more than one, or a significant number, of codons with one or more codons that are more frequently used in the genes of that organism.

Standard recombinant DNA and molecular cloning techniques used here are well known in the art and are described, e.g., by Sambrook et al., Molecular Cloning: A Laboratory Manual, Third Edition, Cold Spring Harbor Laboratory Press, Cold Spring Harbor, N.Y. (2000); and by Silhavy et al., Experiments with Gene Fusions, Cold Spring Harbor Laboratory Press, Cold Spring Harbor, N.Y. (1984); and by Ausubel et al., Current Protocols in Molecular Biology, published by Greene Publishing Assoc. and Wiley Interscience (1987 to present).

DETAILED DESCRIPTION OF THE INVENTION

Part of this invention concerns polypeptides which have geranylgeranyl pyrophosphate synthase activity and thus can be used in genetically modified host cells for the production of GGPP derived terpenoids. In some embodiments, the invention provides a GGPP synthase from *Mucor circinelloides* in a host cell that is not *Mucor circinelloides*, for the over-production of GGPP derived terpenoids as compared with the level produced in an otherwise identical organism not subject to the same modification.

GGPP Synthase

For the purpose of this invention, a polypeptide having GGPP synthase activity is one which enzyme catalyzes the synthesis of GGPP from farnesyl-pyrophosphate (FPP), geranyl-pyrophosphate (GPP), dimethylallyl-pyrophosphate (DMAP) and/or isopentyl-pyrophosphate (IPP).

In one embodiment, a subject GGPP synthase is encoded by a GGPP synthase gene of *Mucor circinelloides*. In some embodiments, a subject nucleic acid comprises the nucleotide sequence set forth in SEQ ID NO: 1. In some embodiments, a subject nucleic acid comprises a nucleotide sequence having at least about 60%, at least about 70%, at least about 80%, at least about 85%, at least about 90%, at least about 95%, at least about 98%, or at least about 99% nucleotide sequence identity to the nucleotide sequence set forth in SEQ ID NO:1.

In some embodiments, a subject nucleic acid comprises a nucleotide sequence encoding a polypeptide comprising an amino acid sequence as set forth in SEQ ID NO:2. In some embodiments, a subject nucleic acid comprises a nucleotide sequence encoding a polypeptide comprising an amino acid sequence having at least about 60%, at least about 70%, at least about 80%, at least about 85%, at least about 90%, at least about 95%, at least about 98%, or at least about 99% amino acid sequence identity to the amino acid sequence set forth in SEQ ID NO:2.

In some embodiments, a subject nucleic acid comprises a nucleotide sequence encoding a polypeptide having an amino acid sequence with substitution, deletion, insertion and/or addition of one or several amino acid residues in the amino acid sequence of SEQ ID NO:2 and the protein having GGPP synthase activity. In some embodiments, the amino acid sequence has one, two, three, four, five, six, seven, eight, nine, ten, from about 10 to about 15, from about 15 to about 20, or from about 20 to about 25 conservative amino acid substitutions compared to the amino acid sequence set forth in SEQ ID NO:2.

In some embodiments, a subject nucleic acid comprises a nucleotide sequence that encodes a variant of a polypeptide comprising an amino acid sequence set forth in SEQ ID NO:2. For example, in some embodiments, a subject nucleic acid comprises a nucleotide sequence encoding an enzyme that exhibits one or more of the following properties compared to an enzyme comprising an amino acid sequence set forth in SEQ ID NO:2: 1) increased enzymatic activity; 2) increased stability in vitro and/or in vivo; 3) increased product yield; 4) altered protein turnover rate; and 5) increased enzyme efficiency (e.g., increased efficiency of substrate conversion to generate product).

Constructs

The present invention further provides recombinant vectors ("constructs") comprising a subject nucleic acid. In some embodiments, a subject recombinant vector provides for amplification of a subject nucleic acid. In some embodiments, a subject recombinant vector provides for production of an encoded GGPP synthase in a eukaryotic cell, in a prokaryotic cell, or in a cell-free transcription/translation system.

Suitable promoters for use in fungal host cell include but are not limited to, a TEF1 promoter, an HSP promoter, a HYP promoter, and an ALK1 promoter.

In many embodiments, a subject recombinant vector comprises a nucleotide sequence encoding an GGPP synthase and is operably linked to a promoter. In some embodiments, a subject recombinant vector comprises a nucleotide sequence encoding a GGPP synthase from *Mucor circinelloides* and is operably linked to a promoter. In some embodiments, a subject recombinant vector comprises a nucleotide sequence encoding a polypeptide comprising an amino acid sequence as set forth in SEQ ID NO:2 and is operably linked to a promoter. In some embodiments, a subject recombinant vector comprises a nucleotide sequence encoding a polypeptide having an amino acid sequence with substitution, deletion, insertion and/or addition of one or several amino acid residues in the amino acid sequence of SEQ ID NO:2 and the nucleotide sequence is operably linked to a promoter. The above polypeptide has GGPP synthase activity.

Host Cells

The present invention provides genetically modified host cells, e.g., host cells that have been genetically modified with the aforementioned subject nucleic acid or subject recombinant vector. In many embodiments, a subject genetically modified host cell is an in vitro host cell. In other embodiments, a subject genetically modified host cell is an in vivo host cell. In other embodiments, a subject genetically modified host cell is part of a multicellular organism.

Host cells are in many embodiments unicellular organisms, or are grown in culture as single cells. In some embodiments, the host cell is a eukaryotic cell. Suitable eukaryotic host cells include, but are not limited to, yeast cells, insect cells, plant cells, fungal cells, and algal cells.

Suitable eukaryotic host cells include, but are not limited to, the cells of genera of *Yarrowia, Saccharomyces, Candida, Aspergillus, Trichoderma, Fusarium, Neurospora, Crypthecodinium, Schizochytrium*, and *Thraustochytrium*, and the like.

In some embodiments of the present disclosure that utilize heterologous isoprenoid biosynthesis polypeptides or carotenogenic biosynthesis polypeptides, the source organisms include, but are not limited to, fungi of the genera *Aspergillus, Blakeslea, Botrytis, Candida, Cercospora, Cryptococcus, Cunninghamella, Fusarium (Gibberella), Kluyveromyces, Lipomyces, Mortierella, Mucor, Neurospora, Penicillium, Phycomyces, Pichia (Hansenula), Puccinia, Pythium, Rhodosporidium, Rhodotorula, Saccharomyces, Sclerotium, Trichoderma, Trichosporon, Xanthophyllomyces (Phafia)*, and *Yarrowia*. In certain embodiments, the source organisms are of a species including, but not limited to, *Aspergillus terreus, Aspergillus nidulans, Aspergillus niger, Blakeslea trispora, Botrytis cinerea, Candida japonica, Candida pulcherrima, Candida revkaufi, Candida tropicalis, Candida utilis, Cercospora nicotianae, Cryptococcus curvatus, Cunninghamella echinulata, Cunninghamella elegans, Fusarium fujikuroi (Gibberella zeae), Kluyveromyces lactis, Lipomyces starkeyi, Lipomyces lipoferus, Mortierella alpina, Mortierella ramanniana, Mortierella isabellina, Mortierella vinacea, Mucor circinelloides, Neurospora crassa, Phycomyces blakesleanus, Pichia pastoris, Puccinia distincta, Pythium irregulare, Rhodosporidium toruloides, Rhodotorula glutinis, Rhodotorula graminis, Rhodotorula mucilaginosa, Rhodotorula pinicola, Rhodotorula gracilis, Saccharomyces cerevisiae, Sclerotium rolfsii, Trichoderma reesei, Trichosporon cutaneum, Trichosporon pullulans, Xanthophyllomyces dendrorhous (Phaffia rhodozyma), Crypthecodinium cohnii, Schizochytrium sp., Thraustochytrium sp*. and *Yarrowia lipolytica*.

In some embodiments, the host cell is a eukaryotic cell other than a plant cell. In other embodiments, the host cell is a plant cell.

In other embodiments, the host cell is a prokaryotic cell. Suitable prokaryotic cells include, but are not limited to, and gram negative or positive bacterium. Gram-positive bacterial hosts include, but are not limited to, *Bacillus, Brevibacillus, Clostridium, Geobacillus, Lactobacillus, Lactococcus, Paenibacillus*, and *Streptomyces*. Gram-negative bacteria include, but are not limited to *E. coli, Pseudomonas* and *Paracoccus*. The recombinant bacterial host may be any Bacillales including, but not limited to, *Bacillus amyloliquefaciens, Brevibacillus brevis, Bacillus circulans, Bacillus clausii, Bacillus coagulans, Bacillus lentus, Bacillus licheniformis, Geobacillus stearothermophilus, Bacillus subtilis*, and *Bacillus thuringiensis*. The recombinant bacterial host may also be any *Streptomyces* including, but not limited to, *Streptomyces achromogenes, Streptomyces avermitilis, Streptomyces coelicolor, Streptomyces griseus*, and *Streptomyces lividans*.

The recombinant bacterial host may also be any *Paracoccus* including, but not limited to *Paracoccus denitrificans, Paracoccus versutus, Paracoccus carotinifaciens, Paracoccus marcusii*, and *Paracoccus zeaxanthinifaciens*.

To generate a subject genetically modified host cell, a subject nucleic acid comprising the aforementioned subject nucleic acid or subject recombinant vector is introduced stably or transiently into a parent host cell, using established transformation techniques.

In some of the embodiments, the present invention is directed to a genetically modified host organism comprising the aforementioned subject nucleic acid or subject recombinant vector. Such genetically modified host organism may be in the form of a unicellular host cell or multicellular cells.

Genetically Modified Host Cells

In some of the embodiments, the ability of the host cell to produce a terpenoid, which is possessed by the cell before the introduction of the above aforementioned subject nucleic acid or subject recombinant vector, may be a property of the host in its native form, or may be as a result of the introduction of one or more recombinant nucleic acid sequences that involves in the terpenoid biosynthesis pathway.

In the following paragraphs, exemplary genetically modified host cells are described to show the type of terpenoid biosynthesis pathways and the type of terpenoid products which may be affected by the method disclosed in the present invention. Specifically, genetically modified host cells for the synthesis of isoprenoids, carotenoids, ionones, abienol, and sclareol are described. However, these examples should not be construed as limiting in any way about the scope of the present invention, such as the type of terpenoids that can be produced using the methods described in the present invention.

Genetically Modified Host Cells for the Synthesis of Isoprenoids

In some embodiments, a subject genetically modified host cell is a host cell that normally synthesizes isoprenoid via a isoprenoid biosynthesis pathway. The most common isoprenoid biosynthesis pathway is sometimes referred to as the "mevalonate pathway". Briefly, acetyl-CoA is converted, via hydroxymethylglutaryl-CoA (HMG-CoA), into mevalonate. Mevalonate is then phosphorylated and converted into the five-carbon compound isopentenyl pyrophosphate (IPP). Following isomerization of IPP into dimethylallyl pyrophosphate (DMAPP), three sequential condensation reactions with additional molecules of IPP generate the ten-carbon molecule geranyl pyrophosphate (GPP), followed by the fifteen-carbon molecule farnesyl pyrophosphate (FPP), and finally the twenty-carbon compound geranylgeranyl pyrophosphate (GGPP).

An alternative isoprenoid biosynthesis pathway is utilized by some organisms (particularly bacteria and plants) and is sometimes called the "mevalonate-independent pathway" or "non-mevalonate pathway". This pathway is initiated by the synthesis of 1-deoxy-D-xyloglucose-5-phosphate (DOXP) from pyruvate and glyceraldehyde-3-phosphate. DOXP is then converted, via a series of reactions, into IPP, which isomerizes into DMAPP and is then converted, via GPP and FPP, into GGPP.

Various proteins involved in isoprenoid biosynthesis have been identified and characterized in a number of organisms. Moreover, various aspects of the isoprenoid biosynthesis pathway are conserved throughout the fungal, bacterial, plant and animal kingdoms. For example, polypeptides corresponding to the acetoacetyl-CoA thiolase, HMG-CoA synthase, HMG-CoA reductase, mevalonate kinase, phosphomevalonate kinase, mevalonate pyrophosphate decarboxylase, IPP isomerase, FPP synthase, and GGPP synthase have been identified in and isolated from a wide variety of organisms and cells.

Alternatively or additionally, modified mevalonate kinase polypeptides that exhibit decreased feedback inhibition properties (e.g., to farnesyl pyrophosphate (FPP)) may be utilized in accordance with the present disclosure. Such modified mevalonate kinase polypeptides may be of eukaryotic or prokaryotic origin. For example, modified versions of mevalonate kinase polypeptides from animals (including humans), plants, algae, fungi (including yeast), and/or bacteria may be employed; for instance, modified versions of mevalonate kinase polypeptides may be utilized.

In some embodiments, a subject genetically modified host cell comprises one or more polypeptides that is involved in the synthesis of isoprenoids. In some embodiments, such polypeptides include acetoacetyl-CoA thiolase, HMG-CoA synthase, HMG-CoA reductase, mevalonate kinase, phosphomevalonate kinase, mevalonate pyrophosphate decarboxylase, IPP isomerase, FPP synthase, and GGPP synthase. The above enzymes are all involved in the mevalonate pathway for isoprenoid biosynthesis.

Non-limiting examples of genetically modified host cell which comprises one or more polypeptides that is involved in the synthesis of isoprenoids can be found in U.S. patent application Ser. No. 12/937,204, which content is incorporated hereby in its entirety.

The terpenoid biosynthesis pathway may be divided, in one embodiment, into two portions: the upstream isoprenoid biosynthesis pathway, which leads to the formation of GGPP, and the downstream terpenoid pathway, which converts GGPP into long chain C20, C30, or C40 compounds.

The term "upstream isoprenoid biosynthesis pathway" and "upstream pathway" refers, in one embodiment, to the portion of the pathway involved in the synthesis of GGPP, which includes the mevalonate pathway.

The term "downstream terpenoid biosynthesis pathway" or "downstream pathway", refers to the pathways for biosynthesizing the various terpenoid molecules having the common precursor of IPP. GGPP, which is derived from the condensation of one DMAP and three IPP moieties, is the four-subunit precursor for most diterpenoid molecules. Examples of GGPP derivatives produced by the cells and methods of the present invention include, but are not limited to, carotenoids, ionones, abienol, and sclareol.

Genetically Modified Host Cells for the Synthesis of Carotenoids

Figure 1A:
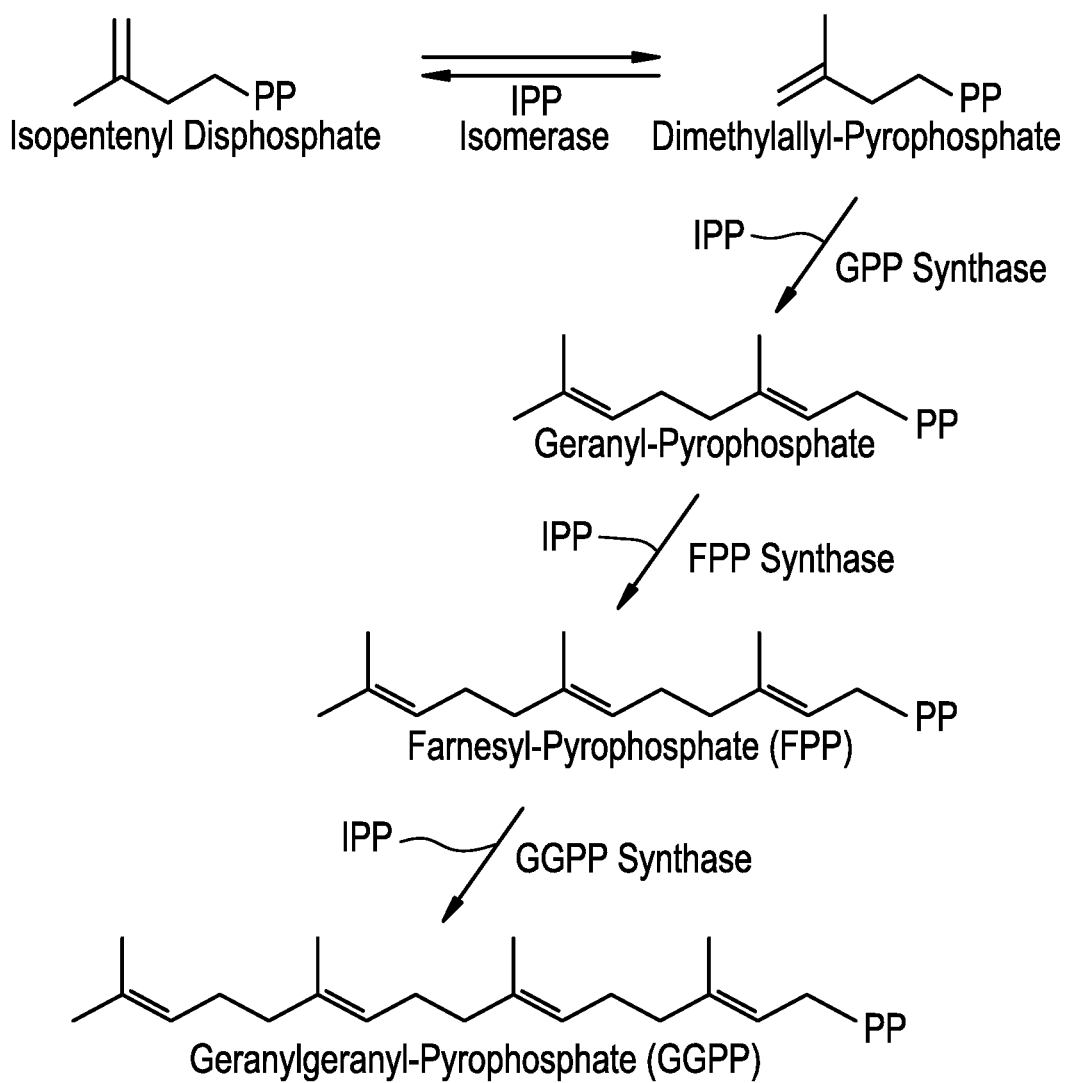
FIG. 1A shows a biosynthetic scheme for geranylgeranyl pyrophosphate (GGPP) production from isopentenyl pyrophosphate (IPP).
Figure 1B:
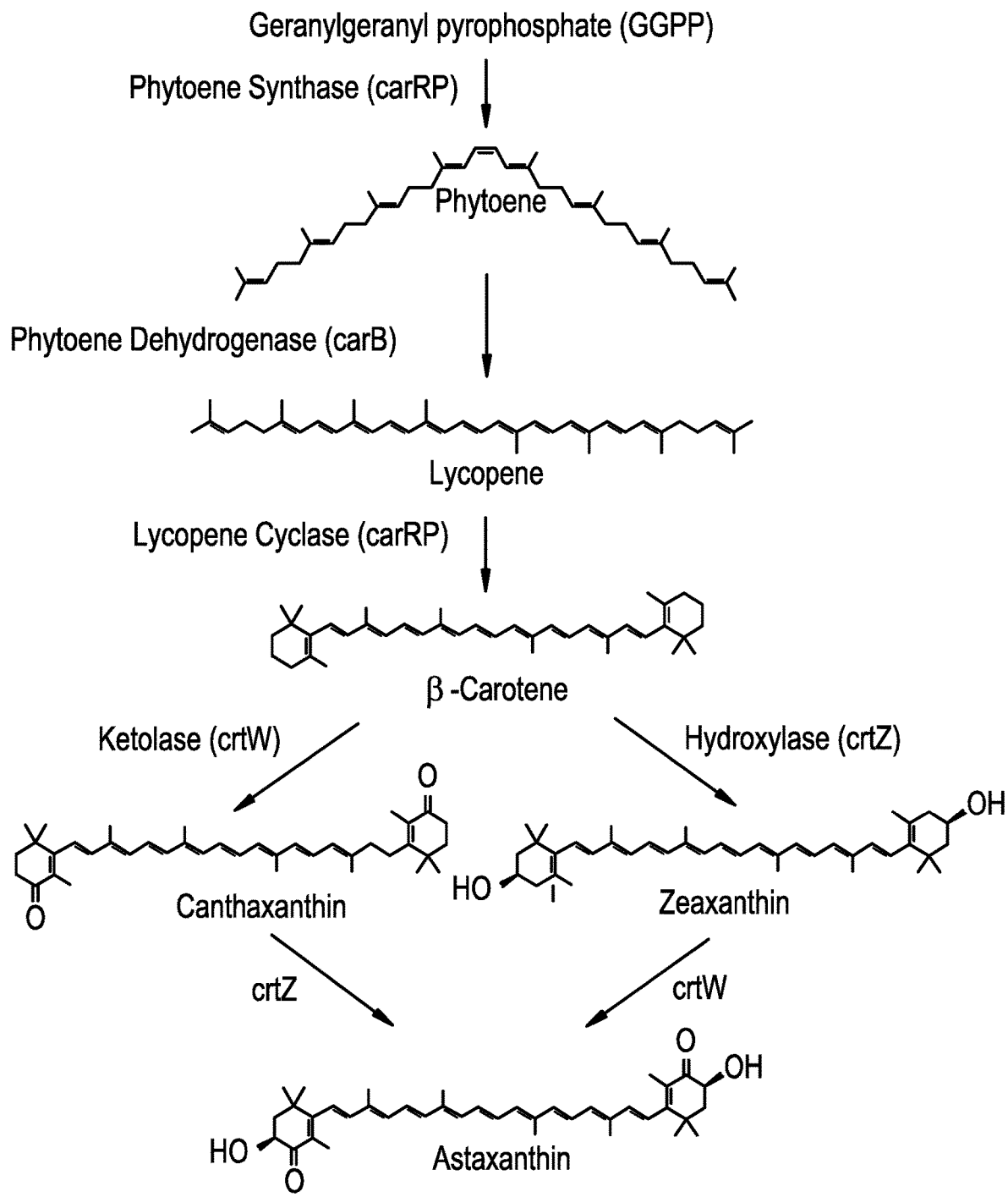
FIG. 1B shows a biosynthetic scheme for conversion of GGPP into various carotenoids.

The carotenoid biosynthesis pathway branches off from the isoprenoid biosynthesis pathway at the point where GGPP is formed. See FIG. 1B. The commitment step in carotenoid biosynthesis is the formation of phytoene by the head-to-head condensation of two molecules of GGPP, catalyzed by phytoene synthase (often called CrtB). A series of dehydrogenation reactions, each of which increases the number of conjugated double bonds, converts phytoene into lycopene. The pathway branches at various points, both before and after lycopene production, so that a wide range of carotenoids can be generated. For example, action of a mono-cyclase enzyme on lycopene generates γ-carotene; over-desaturation may produce 3,4-didehydrolycopene. γ-carotene is converted to β-carotene through the action of a cyclase. β-carotene can be processed into any of a number of products, including astaxanthin (via e.g., chinenone, hydroxyechinenone, and phoenicoxanthin).

According to the present disclosure, carotenoid production in a host organism may be adjusted by modifying the expression or activity of one or more proteins involved in carotenoid biosynthesis. In some embodiments, it will be desirable to utilize as host cells organisms that naturally produce one or more carotenoids. In some such cases, the focus will be on increasing production of a naturally-produced carotenoid, for example by increasing the level and/or activity of one or more proteins involved in the synthesis of that carotenoid and/or by decreasing the level or activity of one or more proteins involved in a competing biosynthetic pathway. Alternatively or additionally, in some embodiments it will be desirable to generate production of one or more carotenoids not naturally produced by the host cell.

According to some embodiments of the disclosure, it will be desirable to introduce one or more heterologous carotenogenic polypeptides into a host cell. As will be apparent to those of ordinary skill in the art, any of a variety of heterologous polypeptides may be employed; selection will consider, for instance, the particular carotenoid whose production is to be enhanced. The present disclosure contemplates not only introduction of heterologous carotenogenic polypeptides, but also adjustment of expression or activity levels of heterologous or endogenous carotenogenic polypeptides.

Proteins involved in carotenoid biosynthesis include, but are not limited to, phytoene synthase, phytoene dehydrogenase, lycopene cyclase, carotenoid ketolase, carotenoid hydroxylase, astaxanthin synthase (a single multifunctional enzyme found in some source organisms that typically has both ketolase and hydroxylase activities), carotenoid epsilon hydroxylase, lycopene cyclase (beta and epsilon versions), carotenoid glucosyltransferase, and acyl CoA:diacyglycerol acyltransferase.

It will be appreciated that the particular carotenogenic modification to be applied to a host cell in accordance with the present disclosure will be influenced by which carotenoid(s) is desired to be produced. For example, isoprenoid biosynthesis polypeptides are relevant to the production of most carotenoids. Carotenoid biosynthesis polypeptides are also broadly relevant. Carotenoid ketolase activity is particularly relevant for production of canthaxanthin, and carotenoid hydroxylase activity is for production of lutein and zeaxanthin, among others. Both carotenoid hydroxylase and ketolase activities (and astaxanthin synthase) are particularly useful for production of astaxanthin.

Non-limiting examples of genetically modified host cells which comprise one or more polypeptides involved in the synthesis of carotenoids can be found in U.S. patent application Ser. No. 12/937,204.

Genetically Modified Host Cells for the Synthesis of Ionones

Figure 1C:
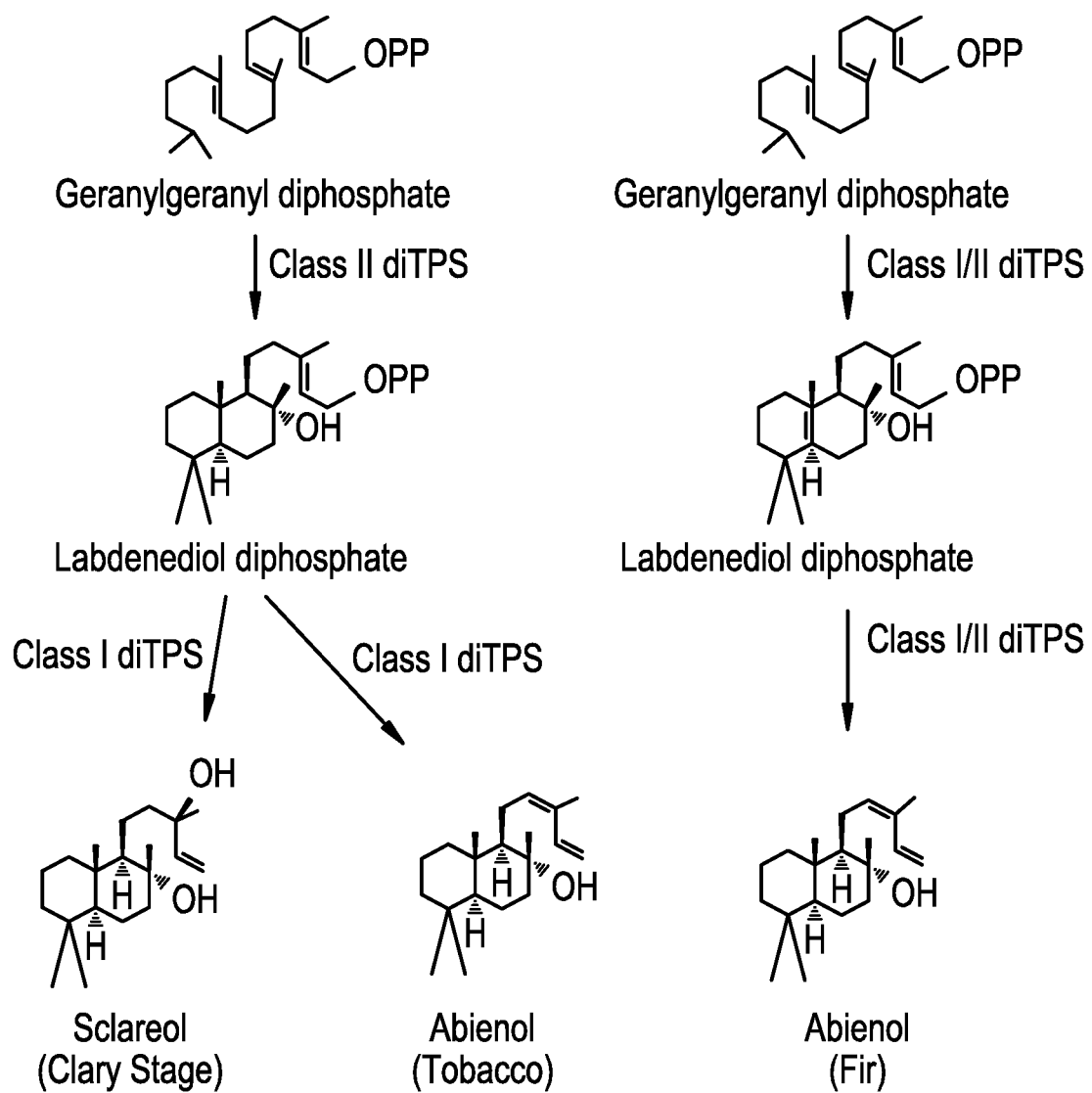
FIG. 1C shows a biosynthetic scheme for conversion of GGPP into abienol and sclareol.
Figure 1D:
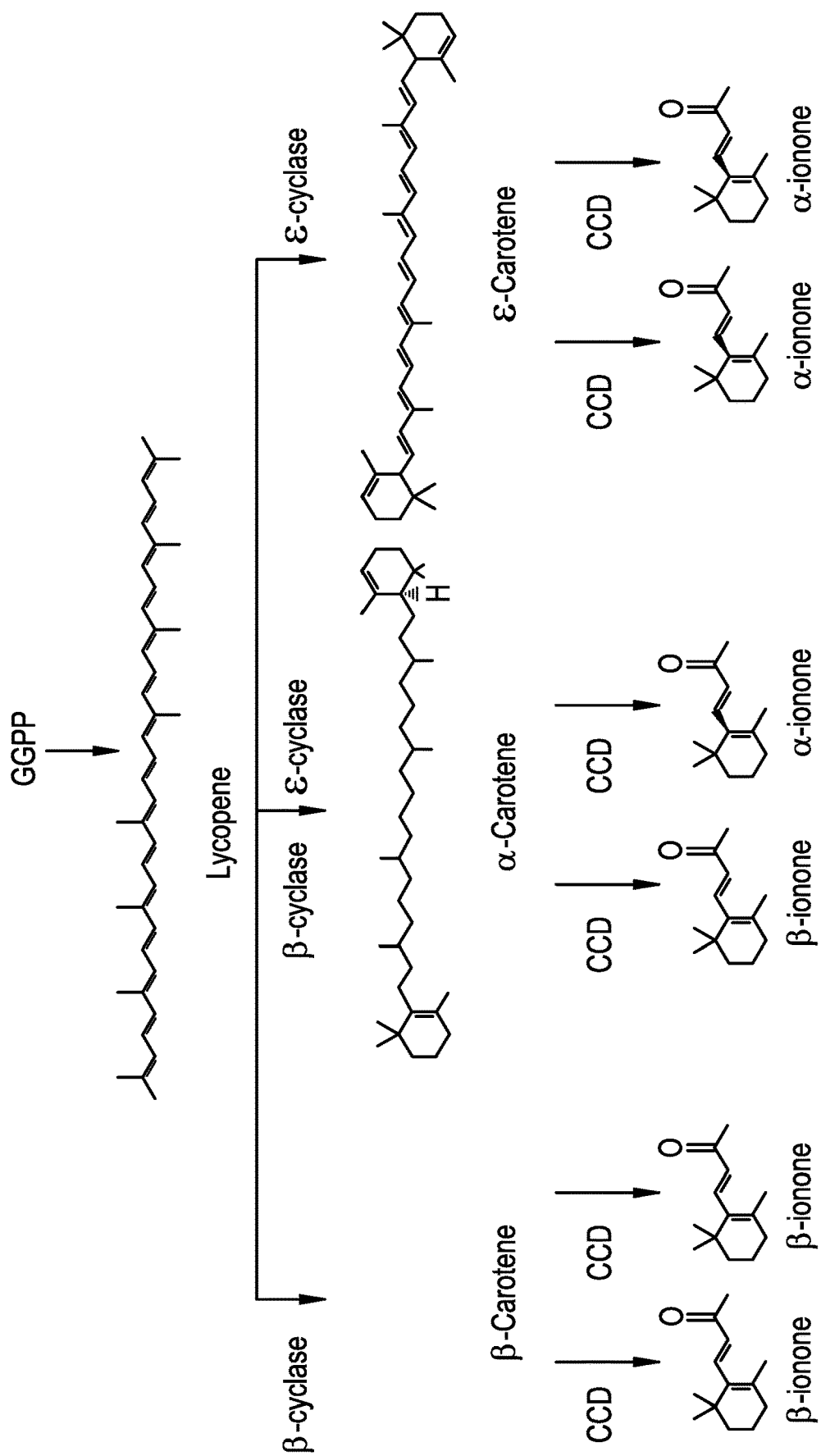
FIG. 1D shows a biosynthetic scheme for conversion of GGPP into ionones.

Ionone compounds are synthesized from carotenoid precursors, which are themselves synthesized from isoprenoid precursors. Thus, any carotenogenic modification that results in the increased production of a carotenoid from which an ionone compound can be produced may similarly result in an increased production of a ionone compound. Ionone compounds comprise β-ionone and α-ionone. In certain embodiments, the β-ionone compound is synthesized from the carotenoid precursor β-carotene and/or α-carotene. In other embodiments, the α-ionone compound is synthesized from the carotenoid precursors ε-carotene and/or α-carotene. See FIG. 1D.

According to the present disclosure, ionone compound production in a host organism may be adjusted by modifying the expression or activity of one or more proteins involved in ionone compound biosynthesis. In some embodiments, it will be desirable to utilize as host cells organisms that naturally produce one or more ionone compounds. Alternatively or additionally, in some embodiments it will be desirable to generate production of one or more ionone compounds not naturally produced by the host cell.

According to some embodiments of the disclosure, it will be desirable to introduce one or more heterologous ionone-synthesis polypeptides into a host cell. As will be apparent to those of ordinary skill in the art, any of a variety of heterologous polypeptides may be employed; selection will consider, for instance, the particular ionone compound whose production is to be enhanced. The present disclosure contemplates not only introduction of heterologous ionone-synthesis polypeptides, but also adjustment of expression or activity levels of heterologous ionone-synthesis polypeptides, including, for example, alteration of constitutive or inducible expression patterns.

Proteins involved in ionone biosynthesis include, but are not limited to, lycopene cyclase (beta and epsilon subunits), and carotenoid cleavage dioxygenase.

Genetically Modified Host Cells for the Synthesis of Abienol and Sclareol

Abienol and sclareol compounds are synthesized from the isoprenoid precursor of GGPP, which is the product of the isoprenoid-synthesis pathway. Thus, any genetic modification that results in the increased production of GGPP from which abienol or sclareol compound can be produced may similarly result in an increased production of an abienol or a sclareol compound.

The pathways to produce both abienol and sclareol are proposed to involve two steps. See FIG. 1C. The first step consists of the conversion of the isoprenoid pathway molecule GGPP to a common intermediate named labda-13-en-8-ol diphosphate (LDPP) through the activity of a class II diterpene synthase (diTPS). The second step is catalyzed by a class I diTPS. There are several type of class I diTPS, each responsible for producing a specific end product. For example, abienol synthase (ABS) is responsible for abienol production, and sclareol synthase (SS) is responsible for sclareol production.

The enzymes involved in the two-step conversion of GGPP to sclareol or GGPP to abienol are plant specific and can be in the form of two independent enzymes or a single enzyme with two active sites. For example, in abienol production by tobacco, the class II diTPS of tobacco and the class I diTPS synthase of tobacco are in the form of two different protein molecules. Similarly, in sclareol production by clary sage, the class II diTPS of clary sage and the class I diTPS synthase of clary sage are also in the form of two independent protein molecules. In contrast, in the production of abienol by fir both class I and class II diTPS subunits reside on one bifunctional class I/II abienol synthase. Therefore in fir, GGPP is converted to abienol in the presence of the single bifunctional class I/II abienol synthase.

According to the present disclosure, abienol or sclareol compound production in a host organism may be adjusted by modifying the expression or activity of one or more proteins involved in the abienol or sclareol compound biosynthesis. In some embodiments, it will be desirable to utilize as host cells organisms that naturally produce one or more abienol or sclareol compound. Alternatively or additionally, in some embodiments it will be desirable to generate production of one or more abienol or sclareol compounds not naturally produced by the host cell.

According to some embodiments of the disclosure, it will be desirable to introduce one or more heterologous abienol-synthesis or sclareol-synthesis polypeptides into a host cell. As will be apparent to those of ordinary skill in the art, any of a variety of heterologous polypeptides may be employed; selection will consider, for instance, the particular abienol or sclareol compound whose production is to be enhanced. The present disclosure contemplates not only introduction of heterologous polypeptides, but also adjustment of expression or activity levels of heterologous polypeptides, including, for example, alteration of constitutive or inducible expression patterns.

Non-limiting examples of genetically modified host cell which comprises one or more polypeptides that is involved in the synthesis of carotenoids can be found in U.S. Patent Application No. 62/089,511, which content is incorporated hereby in its entirety.

Codon Usage

In some embodiments, a nucleotide sequence used to generate a subject genetically modified host cell is modified such that the nucleotide sequence reflects the codon preference for the particular host cell. For example, the nucleotide sequence will in some embodiments be modified for *Yarrowia* codon preference. As another non-limiting example, the nucleotide sequence will in other embodiments be modified for *E. coli* codon preference. As another non-limiting example, the nucleotide sequence will in other embodiments be modified for yeast (*Saccharomyces*) codon preference.

Production and Isolation of Terpenoid Compounds

The present invention provides a method of producing a terpneoid compound. In some embodiments, the methods generally involve culturing a genetically modified host cell in a suitable medium, wherein said host cell is genetically modified with a subject nucleic acid comprising a nucleotide sequence encoding a GGPP synthase enzyme. In one embodiment, the host cell is genetically modified with a subject nucleic acid comprising a nucleotide sequence encoding a GGPP synthase enzyme from *Mucor circinelloides*. In some embodiments, the above host cells are naturally carotenoid-producing or have been engineered to produce carotenoids. In some embodiments, the above host cells are naturally ionone-producing or have been engineered to produce ionones. In some embodiments, the above host cells are naturally abienol-producing or have been engineered to produce abienol. In some embodiments, the above host cells are naturally sclareol-producing or have been engineered to produce sclareol.

Typically, the method is carried out in vivo, although in vitro production of an terpenoid compound is also contemplated. In some of these embodiments, the host cell is a eukaryotic cell, e.g., a *Yarrowia* cell. In other embodiments, the host cell is a prokaryotic cell. In some of these embodiments, the host cell is a plant cell. In some of these embodiments, the host cell is an insect or an animal cell.

In certain embodiments of the disclosure, it will be desirable to accumulate carotenoid compounds in a host cell that is genetically modified with a subject nucleic acid or a subject recombinant vector to levels (i.e., considering the total amount of all produced carotenoid compounds together, or considering a particular carotenoid compound) that are more than 1.5 fold higher than that of an otherwise identical host cell not subject to the same modification. In some embodiments, the total carotenoid compound accumulation will be to a level more than more than 2 fold, more than 3 fold, more than 4 fold, more than 5 fold, more than 6 fold, or more than 7 fold higher in a host cell that is genetically modified with a subject nucleic acid comprising a nucleotide sequence encoding a GGPP synthase enzyme from *Mucor circinelloides* as compared with an otherwise identical host cell not subject to the same modification.

In some embodiments, the particular carotenoid compound accumulated in the above genetically modified host cells include, but are not limited to, antheraxanthin, adonirubin, adonixanthin, astaxanthin, canthaxanthin, capsorubrin, β-cryptoxanthin, α-carotene, β-carotene, β,ψ-carotene, δ-carotene, ε-carotene, echinenone, 3-hydroxyechinenone, 3'-hydroxyechinenone, γ-carotene, γ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, a C30 carotenoid, and combinations thereof.

In certain embodiments of the disclosure, it will be desirable to accumulate ionone compounds in a host cell that is genetically modified with a subject nucleic acid comprising a subject nucleic acid or a subject recombinant vector to levels (i.e., considering the total amount of all produced ionone compounds together, or considering a particular ionone compound) that are more than 1.5 fold higher than that of an otherwise identical host cell not subject to the same modification. In some embodiments, the total carotenoid compound accumulation will be to a level more than 2 fold, more than 3 fold, more than 4 fold, more than 5 fold, more than 6 fold, or more than 7 fold higher in a host cell that is genetically modified with a subject nucleic acid comprising a nucleotide sequence encoding a GGPP synthase enzyme from *Mucor circinelloides* as compared with an otherwise identical host cell not subject to the same modification.

In some embodiments, the particular ionone compound accumulated in the above genetically modified host cells include, but not limited to, α-ionone and β-ionone.

In certain embodiments of the disclosure, it will be desirable to accumulate abienol and/or sclareol compounds in a host cell that is genetically modified with a subject nucleic acid comprising a subject nucleic acid or a subject recombinant vector to levels that are more than 1.5 fold higher than that of an otherwise identical host cell not subject to the same modification. In some embodiments, the total abienol and/or sclareol compound accumulation will be to a level more than more than 2 fold, more than 3 fold, more than 4 fold, more than 5 fold, more than 6 fold, more than 7 fold higher in a host cell that is genetically modified with a subject nucleic acid comprising a nucleotide sequence encoding a GGPP synthase enzyme from *Mucor circinelloides* as compared with an otherwise identical host cell not subject to the same modification.

To give but a few specific examples, the present disclosure provides modified *Y. lipolytica* strains that have been engineered to express the GGPP synthase polypeptide (encoded by carG) from *M. circinelloides*. The *Y. lipolytica* host strain may have been engineered to express the phytoene synthase/lycopene cyclase bifunctional (encoded by carRP) polypeptide from *M. circinelloides*, and also to express the phytoene dehydrogenase (encoded by carB) polypeptide from *M. circinelloides*. In some embodiments, the present disclosure provides such carG-expressing *Y. lipolytica* strains that have been engineered to modify expression and/or activity of a truncated HMG-CoA reductase polypeptide from *Y. lipolytica* and/or one or more *Y. lipolytica* polypeptides selected from the group consisting of GGPP synthase (Ggs1), FPP synthase (Erg20), IPP isomerase (Idi or Idi1), HMG synthase (Erg13), mevalonate kinase (Erg12), squalene synthase (Erg9), phosphimevalonate kinase (Erg8), mevalonate pyrophosphate decarboxylase (Mvd1), malic enzyme, malate dehydrogenase, glucose 6 phosphate dehydrogenase, malate dehydrogenase homolog 2, 6-phosphogluconate dehydrogenase (Gnd1), isocitrate dehydrogenase, fructose 1,6 bisphosphatase, acetoacetyl CoA thiolase (Erg10), ATP citrate lyase subunit 1, ATP citrate lyase subunit 2, and combinations thereof. The present disclosure therefore, in one embodiment, specifically provides *Y. lipolytica* strain that is genetically engineered to enhance the production of GGPP and thus causes enhanced carotenoid production (and of other isoprenoids), wherein said that the *Y. lipolytica* host strain has been engineered to produce carotenoids.

In some embodiments, a subject genetically modified host cell is cultured in a suitable medium (e.g. YPD broth, etc.); and the culture medium is overlaid with an organic solvent, e.g. dodecane, forming an organic layer. The terpenoid compound produced by the genetically modified host cell partitions into the organic layer, from which it can be purified. In some embodiments, where the terpenoid-biosynthesis enzyme-encoding nucleotide sequence is operably linked to a promoter, and, after a suitable time, the terpenoid compound is isolated from the organic layer overlaid on the culture medium.

The process for the production of a terpenoid according to the present invention may be carried out in any suitable fermentation conditions. In one embodiment, such a process may be carried out on an industrial scale.

In some embodiments, the terpenoid compound will be separated from other products which may be present in the organic layer. Separation of the terpenoid compound from other products that may be present in the organic layer is readily achieved using, e.g., standard chromatographic techniques.

Use

Carotenoids compounds produced according to the present disclosure can be utilized in any of a variety of applications, for example, exploiting their biological or nutritional properties (e.g., anti-oxidant, anti-proliferative, etc.) and/or their pigment properties. For example, according to the present disclosure, carotenoids may be used in pharmaceuticals, foodstuff, dietary supplements, electro-optic applications, animal feed additives, cosmetics, etc.

Ionone, abienol and sclareol compounds produced according to the present disclosure can be utilized in applications exploiting their fragrance properties. For example, according to the present disclosure, the ionone, abienol and sclareol compounds may be used in cosmetics, cleaning agents, air-refreshing products, etc.

It will be appreciated that, in some embodiments of the disclosure, carotenoid compounds produced by manipulated host cells as described herein are incorporated into a final product (e.g., food or feed supplement, pharmaceutical, cosmetic, dye-containing item, etc.) in the context of the host cell. For example, host cells may be lyophilized, freeze dried, frozen or otherwise inactivated, and then whole cells may be incorporated into or used as the final product. The host cell may also be processed prior to incorporation in the product to increase bioavailability (e.g., via lysis). Alternatively or additionally, a final product may incorporate only a portion of the host cell (e.g., fractionated by size, solubility), separated from the whole. For example, in some embodiments of the disclosure, lipid droplets are isolated from the host cells and are incorporated into or used as the final product. In other embodiments, the carotenoid compounds themselves, or individual carotenoid compounds are isolated and reformulated into a final product.

In some embodiments of the disclosure, one or more produced carotenoid compounds is incorporated into a component of food or feed (e.g., a food supplement). Types of food products into which carotenoid compounds can be incorporated according to the present disclosure are not particularly limited, and include beverages such as milk, water, sports drinks, soft drinks, energy drinks, teas, juices, and liquors; confections such as jellies and biscuits; fat-containing foods and beverages such as dairy products; processed food products such as rice and soft rice (or porridge); infant formulas; breakfast cereals; or the like. In some embodiments, one or more produced carotenoid compounds is incorporated into a dietary supplements, such as for example a multivitamin. In certain embodiments, β-carotene produced according to the present disclosure is included in a dietary supplement. In certain embodiments, lutein produced according to the present disclosure is included in a dietary supplement. In some embodiments of this aspect of the disclosure, it may be useful to incorporate the carotenoid compounds within bodies of edible lipids as it may facilitate incorporation into certain fat-containing food products.

Examples of feedstuffs into which carotenoid compounds produced in accordance with the present disclosure may be incorporated include, for instance, pet foods such as cat foods, dog foods and the like, feeds for aquarium fish, cultured fish or crustaceans, etc., feed for farm-raised animals (including livestock and further including fish or crustaceans raised in aquaculture). Food or feed material into which the carotenoid compound(s) produced in accordance with the present disclosure is incorporated is preferably palatable to the organism which is the intended recipient. This food or feed material may have any physical properties currently known for a food material (e.g., solid, liquid, soft).

In some embodiments, feedstuffs containing carotenoid compounds produced in accordance with the present disclosure are substantially free of intact host cells.

In some embodiments of the disclosure, one or more produced carotenoid and/or fragrance compounds such as ionone, abienol and sclareol are incorporated into a cosmetic product. Examples of such cosmetics include, for instance, skin cosmetics (e.g., lotions, emulsions, creams and the like), lipsticks, anti-sunburn cosmetics, makeup cosmetics, fragrances, products for daily use (e.g., toothpastes, mouthwashes, bad breath preventive agents, solid soaps, liquid soaps, shampoos, conditioners), etc.

Carotenoid compounds produced according to the present disclosure may be incorporated into any pigment-containing product. They may also be incorporated into a product which is an environmental indicator, or an instrument such as a biosensor for use as a detection agent.

The following Examples are provided to illustrate the present invention, and should not be construed as limiting thereof.

EXAMPLES

Example 1

Construction of Vectors Containing the GGPP Synthase Gene from *Mucor circinelloides* (carG Gene)

Plasmids that were constructed and used in the present disclosure are shown in Table 1.

TABLE 1

| Plasmids | | | |
|---|---|---|---|
| Plasmid | Backbone | Insert | Promoter |
| pMB6157 | HygR | | TEF1 |
| pMB7278 | pUC57 | Synthesized NheI - MluI carG fragment from *M. circinelloides* | |
| pMB7280 | pMB6157 (HygR) | Synthesized NheI - MluI carG fragment from *M. circinelloides* | TEF1 |
| pMB7311 | pMB7280 (HygR) | Synthesized ALK1 promoter | ALK1 |
| pMB6502 | pMB6157 (HygR) | Synthesized NheI - MluI GGS1 fragment from *Y. lipolytica* | TEF1 |
| pMB6200 | pMB6157 | Nat resistance marker | TEF1 |
| pMB6522 | pMB6502 | NatR marker from pMB6200 | TEF1 |
| pMB7322 | pMB7280 | NatR marker from pMB6200 | TEF1 |
| pMB5789 | pMB6157 (Hyg$^R$) | Synthesized NheI - MluI GGS1 fragment from *Y. lipolytica* | TEF1 |
| pMB7280 | pMB6157 (Hyg$^R$) | Synthesized NheI - MluI carG fragment from *M. circinelloides* | TEF1 |
| pMB5992 | pMB4603 (LEU2) | carB and carRP fragments from *M. circinelloides* | TEF1 |
| pMB7380 | pD1218 (G418R 2μ) | Synthesized carG fragment from *M. circinelloides* | TEF1 |
| pMB7381 | pD1218 (G418R 2μ) | Synthesized carG fragment from *M. circinelloides* | TEF1 |
| pMB7382 | pD1218 (G418R 2μ) | BTS1 fragment from *S. cerevisiae* | TEF1 |

The starting plasmid is pMB6157, which contains the TEF1 promoter and XPR2 terminator, and confers hygromycin resistance. The carG gene from *Mucor circinelloides*, cloned in a DNA fragment flanked by NheI on the 5' end, and MluI on the 3' end, was introduced into plasmid pMB6157 to create pMB7278. The above *Mucor circinelloides* carG gene has been codon optimized for *Yarrowia*.

Plasmid pMB7311 was constructed by replacing the TEF1 promoter of MB7280 with 1.0 kb of the *Yarrowia* ALK1 promoter.

Plasmid pMB6502 was constructed by introducing the GGS1 fragment of *Yarrowia* into plasmid pMB6157.

Plasmid pMB6522 was generated from MB6502 by replacing the hygromycin resistance marker with the nourseothricin resistance marker. The nourseothricin resistance marker was derived from *Streptomyces noursei* and was cloned in plasmid pMB6200.

Plasmid pMB7322 was created by replacing the hygromycin resistance marker in plasmid pMB7280 with the nourseothricin resistance marker (NatR) from MB6200.

Strains used in the present invention were previously genetically modified to produce various terpenoids.

Strains listed in Table 2 below are the *Yarrowia lipolytica* and *Saccharomyces cerevisiae* strains used in Examples 2-6. The numbers in parentheses indicate copy number of that gene:

TABLE 2

Strains

| Strain Name | Genotype | Product |
|---|---|---|
| ML7788 | MATA erg9-4789::ura3 GGS1(3) carRP(3) HMG-tr (3) carB(4) (UV mutant) | β-carotene |
| ML15449 | MATA erg9-4789::ura3 GGS1(3) carRP(3) HMG-tr (3)carB(4) alk1Δ alk2Δ PhCCD1(3) | β-ionone |
| ML13149 | MATA erg9-4789::ura3 GGS1 HMG-tr carB AbCAS NtCPS2 ura3 ade1 | Abienol |
| ML10709 | MATA ura3 leu2 URA3-LEU2-4662 prototroph | GGPP |
| ML13509 | MATB ura2fs ade1 leu2 LEU2-carB-carRP-5992 | β-carotene |
| MY278 | MATA ura3 leu2 trp1 (W303) | GGPP |

All *Yarrowia* transformations were carried out via a lithium acetate/PEG fungal transformation protocol method and transformants were selected on YPD+100 μg/ml nourseothricin or YPD+100 μg/ml hygromycin, as appropriate.

All basic molecular biology and DNA manipulation procedures described herein are generally performed according to standard recombinant and molecular cloning techniques.

Example 2

CarG Expression Results in Increased GGPP in *Yarrowia lipolytica*

A wild type *Yarrowia lipolytica* strain, ML10709, was transformed with a integrative linearized DNA fragment containing hygromycin resistance and the TEF1 promoter and XPR2 terminator for expression of DNA encoding GGPP synthases from *Yarrowia lipolytica* and *Mucor circinelloides*, respectively.

The *Yarrowia lipolytica* GGS1 gene, in a HindIII/XbaI fragment from plasmid pMB5789, was compared to the *Mucor circinelloides* carG gene, in a PvuII fragment from plasmid pMB7280, after transformation into an appropriate host. Single colony clonal isolates were examined after two days of growth in YP liquid media containing 5% glucose by growing on a 250 rpm rotary shaker at 30° C. with 20 ml broth in 125 ml baffled flasks. A 2 ml aliquot of broth was immediately spun at 13,000 rpm for 10 seconds, the broth was decanted and 1 ml of 60% hot, 78° C., ethanol water mixture was added to the pellet, vortexed, and incubated for 15 minutes at 78° C. in a heated water bath. The samples were clarified by centrifugation and examined for GGPP using reverse phase LCMS. At least three technical replicates were averaged for each value.

Figure 2:
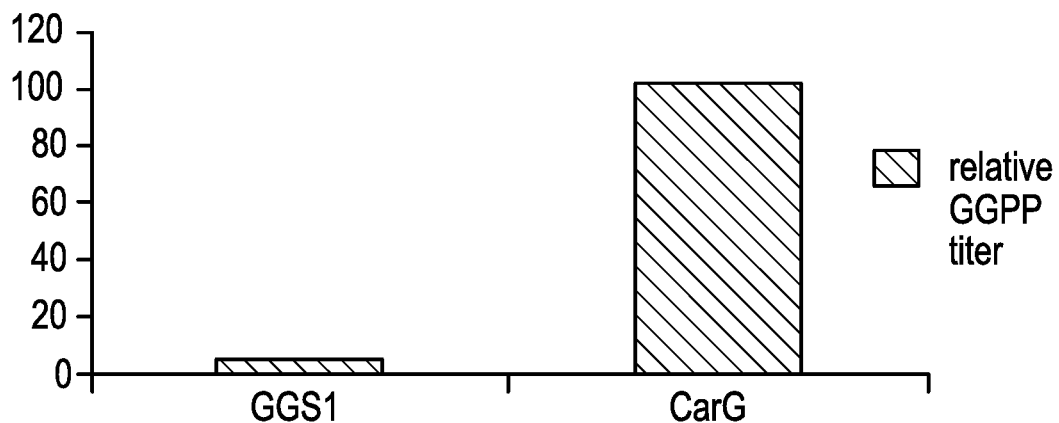
FIG. 2 shows the comparison of GGPP production in a *Yarrowia* strain overexpressing either the GGS1 gene from *Yarrowia lipolytica* or the carG gene from *Mucor circinelloides*.

Quantification of GGPP by HPLC-MS consisted of a Waters XBridge C18 column (3.5 mm, 2.1×50 mm) and an Alliance 2795 HPLC (Waters). The mobile phase was a 20 minute gradient from 20 mM ammonium acetate with 0.1% triethyamine in water to 2 mM ammonium acetate 20:80 acetonitrile:water with 0.1% triethyamine at a flow rate of 0.3 ml/min. The mass spectrometer was run in negative ion mode-MS-MS parent to daughter transition 449.4 mu to 79.0 mu eluting at 14.1 minutes for GGPP. As shown in FIG. 2, a *Yarrowia lipolytica* strain transformed with the *Mucor circinelloides* carG gene resulted in a significantly higher production of GGPP than in the comparable *Yarrowia lipolytica* strain with the overexpressed native GGS1 gene.

Example 3

CarG Expression Results in Increase in Total Carotenoid Titer in *Yarrowia Lipolytica*

A wild type *Yarrowia lipolytica* strain was transformed using nutritional markers for the selection of cassettes containing TEF1 driven carB (*M. circinelloides* phytoene desaturase) and carRP (*M. circinelloides* phytoene synthase-lycopene cyclase) to generate the carotenoid producing *Yarrowia lipolytica* strain, ML13509. ML13509 was transformed with a TEF1 driven *Yarrowia lipolytica* GGS1 gene from plasmid pMB5789 cut with HindIII/XbaI and selected on hygromycin plates. The same β-carotene producing *Yarrowia lipolytica* strain ML13509 was also transformed with the *M. circinelloides* carG gene from plasmid pMB7280 cut with PvuII. The two resulting strains were compared for their carotenoid production level.

In the experiment, single colony clonal isolates were inoculated to 0.8 mL YPD in 24 well shake plates and grown 4 days at 30° C. with shaking at 800 rpm in an Infors device. The cultures were extracted with THF and the cells disrupted by bead beating, and then the samples were analyzed for total carotenoids by HPLC. At least 8 technical replicates where averaged to give the measurement.

Quantification of Carotenoids by HPLC

An Alliance 2795 HPLC (Waters) equipped with a Waters XBridge C18 column (3.5 mm, 2.1×50 mm) and Thermo Basic 8 guard column (2.1×10 mm) was used to resolve compounds at 25° C.; authentic samples of carotenoids (lycopene and β-carotene) were used as standards. The mobile phases and flow rates are shown below (Solvent A=Ethyl Acetate; Solvent B=Water; Solvent C=Methanol; Solvent D=Acetonitrile). The injection volume was 10 μL. The detector is a Waters 2996 photodiode array detector. Wavelength collected was 475 nm for carotenes. The retention times for molecules were at 475 nm and include lycopene (3.53 min), γ-carotene (3.62 min), and β-carotene (3.8 min).

TABLE 3

| HPLC Mobile Phase Gradient Conditions | | | | | | |
|---|---|---|---|---|---|---|
| Time | Flow | % A | % B | % C | % D | Curve |
| 0.01 | 0.5 | 0 | 20 | 0 | 80 | 6 |
| 3 | 1 | 20 | 0 | 0 | 80 | 6 |
| 4.5 | 1 | 80 | 0 | 20 | 0 | 6 |
| 5 | 0.9 | 0 | 0 | 100 | 0 | 6 |
| 6 | 0.9 | 0 | 0 | 100 | 0 | 6 |
| 6.5 | 0.9 | 0 | 20 | 0 | 80 | 6 |
| 7 | 0.5 | 0 | 20 | 0 | 80 | 6 |
| 10 | 0.5 | 0 | 20 | 0 | 80 | 11 |

As shown in FIG. 3, transformants of the *Yarrowia lipolytica* strain receiving the *Mucor circinelloides* carG gene produced significantly higher levels of carotenoids than transformants receiving the native GGS1 gene.

Example 4

CarG Expression Results in Increased GGPP in *Saccharomyces cerevisiae*

A wild type *Saccharomyces cerevisiae* strain, MY278, was transformed with a 2 micron high copy plasmid containing a geneticin (G418) resistance marker (kanMX), and the TEF1 promoter and CYC1 terminator for expression of DNA encoding one of three different GGPP synthases. The three GGPP synthases genes are: *Saccharomyces cerevisiae* BTS1 gene (in plasmid pMB7382), yeast codon optimized *Yarrowia lipolytica* GGS1 gene (in plasmid pMB7381), and the yeast codon optimized *Mucor circinelloides* carG gene (in plasmid pMB7380). The three plasmids were transformed into the host *Saccharomyces cerevisiae* cell. A single colony was isolated, and was examined for GGPP.

The GGPP levels of the host cells with different GGPP synthases were assayed in YP media with 5% glucose after growth in a 250 rpm rotary shaker at 30° C. with 20 ml broth in 125 ml baffled flasks after two days of growth. The broth in a volume of 2 ml was taken out of the shake flask and immediately spun at 13K rpm for 10 seconds. The broth was decanted and 1 ml of a 78° C. 60% ethanol/water mixture was added to the pellet within the tube, vortexed and incubated for 15 minutes at 78° C. in a heated water bath. The samples were cleared by centrifugation and examined for GGPP using reverse phase LCMS as previously described in Example 2. At least two technical replicates were averaged to give the measurement.

As shown in FIG. 4, a *Saccharomyces cerevisiae* strain transformed with the *Mucor circinelloides* carG gene produced a significantly higher level of GGPP than the *Saccharomyces cerevisiae* strain transformed with a *Yarrowia* GGS1 gene or the *Saccharomyces* BTS1 gene.

Example 5

Effect of carG Expression on β-Carotene Production

In this example, a plasmid containing the carG gene of *Mucor circinelloides* was introduced into a host strain of *Y. lipolytica* which had been genetically engineered to produce β-carotene. The relative titer of the β-carotene produced by the new recombinant host cells is analyzed.

The β-carotene producing *Yarrowia* strain ML7788 is a UV mutant of strain ML5252. Strain ML5252 was constructed by the introduction of heterologous genes under the control of constitutive promoters, coupled with several generations of crossbreeding, starting with strain ML350 and ATCC201249 as described in U.S. Pat. No. 7,851,199 (See Table 2 of the patent). The GGS1 gene, erg9 knockdown ("erg9-4789::ura3") and the truncated HMG gene ("HMG-tr") were derived from *Yarrowia* sequences corresponding to native GGPP synthase, squalene synthase, and hydroxymethylglutaryl-CoA reductase genes, respectively. The carRP and carB genes were derived from *Mucor circinelloides*, each encoding a bifunctional phytoene synthase/lycopene cyclase and a phytoene dehydrogenase, respectively.

Plasmid pMB7311, which contains the carG gene of *Mucor circinelloides* and is driven by the ALK1 promoter with hygromycin selection, was linearized and transformed into strain ML7788 to generate strain ML15710. In order to demonstrate the effect of carG expression on the production of β-carotene under fermentor conditions, the strains were grown using a fed-batch process conducted in a bench-scale fermentor. The initial batch phase medium contained 92 g/L corn oil as the primary carbon source. After the initial batch corn oil had been consumed, a rapid rise in the fermentor dissolved oxygen level was observed. At that time, a feed of corn oil was started, with the feed addition rate controlled to maintain the fermentor dissolved oxygen level at 20% of saturation. An aliquot of 25 μL was sampled at time points indicated in FIG. 5 and carotenoids extracted as above.

β-carotene levels were analyzed as follows: an appropriate volume of biomass was added into 2 mL Precellys® lysing tube (tough micro-organism lysing kit #VK05) prefilled with 0.5 mm glass beads. An adjusted volume of extraction solvent (1:1 v/v Heptane/Ethyl Acetate containing 0.01% buytlhydroxytoluene (BHT)) was added to the Precellys® lysing tube up to 1 mL total liquid volume. Lysing tubes were frozen at −80° C. for 10 minutes prior to agitation. Agitation occurred in a Precellys®24 at speed 6500 rpm for 15 seconds, for 3 cycles. After agitation the mixture was spun at maximum speed for 1 min, then transferred to a HPLC vial for analysis. Throughout the protocol, care was taken to avoid contact with oxygen, light, heat, and acids. Quantification of carotenoids by HPLC was the same as in Example 3.

As shown in FIG. 5, introduction of the carG gene of *Mucor circinelloides* increased the production level of β-carotene by approximately 100% (2-fold).

Example 6

Effect of carG Expression on β-Ionone Production

In this example, a vector containing the GGPP synthase carG gene of *M. circinelloides* was introduced into a host strain of *Y. lipolytica* which produces β-ionone, and the relative titer of the β-ionone produced by the recombinant host cells was analyzed.

The β-ionone-producing *Yarrowia* strain ML15449 was constructed from strain ML5252 (see Examples 1 and 2) by the deletion of *Yarrowia* ALK1 and ALK2 genes, followed by introduction of 3 copies of *Yarrowia* codon optimized the *Petunia* CCD1 gene. The *Petunia* CCD1 gene was driven by the TEF1 promoter. Strain ML15699 was generated from ML15449 by transformation with linearized plasmid pMB73 containing the carG gene driven by the ALK1 promoter with hygromycin selection. Strains ML15449 and ML15699 were grown using a fed-batch process conducted in a bench-scale fermentor. The fermentation process for the production of β-ionone was a 2-phase process, with an organic second phase present as 20% of the total initial fermentation batch volume. The initial batch phase medium contained 50 g/L glucose as the primary carbon source. After the initial batch glucose had been consumed, a rapid rise in the fermentor dissolved oxygen level was observed. At that time, a feed of corn oil was started, with the feed addition rate controlled to maintain the fermentor dissolved oxygen level at 20% of saturation. An aliquot of 25 µL was sampled at time points indicated in FIG. 6 and carotenoids and β-ionone were extracted as above.

β-ionone levels were analyzed as follows: an appropriate volume of biomass was added into a bead-pre-filled Precellys® lysing tube as above. An adjusted volume of extraction solvent (1:1 v/v Heptane/Ethyl Acetate containing 0.01% buytlhydroxytoluene (BHT)) is added to a Precellys® lysing tube up to 1 mL total liquid volume. Lysing tubes were frozen at −80° C. for 10 minutes prior to agitation. Agitation occurred in Precellys®24 at speed 6500 rpm for 15 seconds and 3 cycles. After agitation the mixture was spun at maximum speed for 1 min, then transferred to a HPLC vial for analysis. Throughout the protocol, care was taken to avoid contact with oxygen, light, heat, and acids.

The quantification of ionone by HPLC was identical to Example 3 except the wavelength collected was 296 nm for β-ionone and the retention time was 0.58 mins.

As shown in FIG. 6, introduction of the carG gene of Mucor circinelloides increased the production level of β-ionone by over 100% (over 2-fold).

Example 7

Effect of carG Expression on Abienol Production

The abienol-producing Yarrowia strain ML13149 was generated from strain ML7206. Strain ML7206 is derived from a spore resulting from a cross between ML5252 (Table 2) and a MATB strain lacking carRP. Strain ML7206 was transformed with both an Ab-CAS gene (encoding abienol synthase from Abies balsamea) and a Nt-CPS2 gene (encoding a class II diterpene synthase from Nicotiana tabacum). Both the Ab-CAS and Nt-CPS2 genes were codon optimized for expression in Yarrowia.

Strain ML13149 was further transformed with either plasmid pMB7322 (containing the carG gene from Mucor circinelloides), the plasmid pMB6532 (containing the GGS1 gene from Yarrowia lipolytica), or the control plasmid pMB6200 (which lacks a gene encoding GGPP synthase).

Transformants were grown in 24 well plates (Multitron, 30° C., 800 RPM) in YPD media with 20% dodecane for 4 days. The dodecane fraction was removed from the shake plate wells and analyzed by HPLC on a C18 column, with a photo-diode array detector. The HPLC set-up consisted of a YMC PackPro C18 RS column [part #RS08503-1456WT 150×4.6 mm S3 µm] at a column temperature of 16° C., mobile phase consisted of a mixture of 400 mL Methanol, 100 mL Ethanol, and 0.1% Trifluoro-Acetic Acid using an isocratic flow rate of 1.0 mL/min. Abienol was quantitated versus a standard curve with standard at 237 nm and eluted at 3.0 minutes.

The quantification of abienol by HPLC was identical to Example 3 except the wavelength collected was 395 nm for rosafluene and the retention time was 0.43 mins.

As shown in FIG. 7, the production of abienol was enhanced by 4-5-fold in carG containing strains as compared with the level produced in an otherwise identical organism overexpressing the Yarrowia GGS1 gene.

What is claimed is:

1. A process for the production of a terpenoid derived from geranylgeranyl pyrophosphate (GGPP) selected from ionone, sclareol and abienol, comprising cultivating a genetically modified microorganism in a suitable medium and under suitable fermentation conditions to produce the terpenoid, wherein the genetically modified microorganism
   (a) is a yeast;
   (b) comprises a non-endogenous polynucleotide molecule encoding a GGPP synthase, wherein said polynucleotide molecule is selected from the group consisting of:
      (i) a nucleic acid molecule comprising a polynucleotide sequence encoding a protein having the amino acid sequence of SEQ ID NO:2; and
      (ii) a nucleic acid molecule comprising a polynucleotide sequence encoding a protein having at least 90% identity to the amino acid sequence of SEQ ID NO:2; and
   (c) further comprises
      (1) a recombinant nucleotide sequence encoding a carotenoid cleavage dioxygenase, wherein the genetically modified microorganism is capable of producing ionone;
      (2) a recombinant nucleotide sequence encoding a class II diterpene synthase and a recombinant nucleotide sequence encoding a class I diterpene synthase capable of producing sclareol or abienol, wherein the genetically modified microorganism is capable of producing sclareol or abienol; and
      (3) a recombinant nucleotide sequence encoding a class I/II diterpene synthase capable of producing sclareol or abienol, wherein the genetically modified microorganism is capable of producing sclareol or abienol.

2. The process according to claim 1, further comprising the step of incorporation of the terpenoid into a food, feed, fragrance or cosmetic product.

3. The process according to claim 1, wherein the genetically modified microorganism is capable of producing ionone—and further comprises at least one recombinant nucleotide sequence encoding at least one polypeptide selected from the group consisting of:
   (1) a phytoene synthase;
   (2) a phytoene dehydrogenase;
   (3) a lycopene beta-cyclase; and
   (4) a lycopene epsilon-cyclase.

4. The process according to claim 1, further comprising separating the terpenoid from the medium.

5. The process according to claim 1, wherein the yeast is *Yarrowia* or *Saccharomyces*.

6. The process according to claim 1, wherein the genetically modified microorganism is capable of producing ionone and wherein the carotenoid cleavage dioxygenase is *Petunia* CCD1.

7. The process according to claim 1, wherein the class I diterpene synthase is *A. balsamea* CAS and the class II diterpene synthase is *N. tabacum* CPS2.

8. The process according to claim 5, wherein the yeast is *Saccharomyces cerevisiae*.

9. The process according to claim 5, wherein the yeast is *Yarrowia lipolytica*.

* * * * *